US010254910B2

(12) United States Patent
Kawanaka

(10) Patent No.: US 10,254,910 B2
(45) Date of Patent: Apr. 9, 2019

(54) DISPLAY DEVICE AND IMAGE DISPLAY SYSTEM

(71) Applicant: GE Medical Systems Global Technology Company, LLC, Waukesha, WI (US)

(72) Inventor: Tatsuo Kawanaka, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 447 days.

(21) Appl. No.: 14/764,496

(22) PCT Filed: Jan. 24, 2014

(86) PCT No.: PCT/US2014/012991
§ 371 (c)(1),
(2) Date: Jul. 29, 2015

(87) PCT Pub. No.: WO2014/120573
PCT Pub. Date: Aug. 7, 2014

(65) Prior Publication Data
US 2015/0370418 A1    Dec. 24, 2015

(30) Foreign Application Priority Data
Jan. 29, 2013  (JP) .................................. 2013-014405

(51) Int. Cl.
*G09G 5/14* (2006.01)
*G06F 17/30* (2006.01)
(Continued)

(52) U.S. Cl.
CPC .......... *G06F 3/0481* (2013.01); *G06F 3/0482* (2013.01); *G06F 3/0486* (2013.01);
(Continued)

(58) Field of Classification Search
None
See application file for complete search history.

(56) References Cited

U.S. PATENT DOCUMENTS 8,397,170 B2    3/2013  Araoka
8,881,048 B2 *  11/2014 Bakhash ............. G06F 3/04815
                                                          715/764
(Continued)

FOREIGN PATENT DOCUMENTS

JP      2004246582 A    9/2004
JP      2004537810 A    12/2004
(Continued)

OTHER PUBLICATIONS

Unofficial English Translation of Japanese Office Action issued in connection with corresponding JP Application No. 2013014405 dated Jun. 1, 2015.
(Continued)

*Primary Examiner* — Toan H Vu
(74) *Attorney, Agent, or Firm* — Amin, Turocy & Watson, LLP

(57) ABSTRACT

Problem: A display device and an image display system are provided which can easily identify different kinds of windows. Solution: A list X of simplified images M is based on data containing associated information of multiple attributes as metadata. A display is provided to display the list X in a matrix in which the simplified images M are located for respective pieces of associated information of one attribute in a row direction while the simplified images M are located for respective pieces of associated information of another attribute in a column direction. The display has a first sub window SW1 and a second sub window SW2 that are displayed in different display modes on the list X, the first sub window SW1 containing the images M sharing the associated information of one attribute and the associated (Continued)

information of another attribute in the list X of the images M, the second sub window SW2 containing the images M placed in the same folder in the list X of the images M.

18 Claims, 22 Drawing Sheets

(51) Int. Cl.
    *G06F 19/00*         (2018.01)
    *G06F 3/0481*      (2013.01)
    *G06F 3/0482*      (2013.01)
    *G06F 3/0486*      (2013.01)

(52) U.S. Cl.
    CPC .... *G06F 17/3028* (2013.01); *G06F 17/30274* (2013.01); *G06F 19/321* (2013.01); *G09G 5/14* (2013.01); *G09G 2380/08* (2013.01)

(56) References Cited

U.S. PATENT DOCUMENTS

| | | | | |
|---|---|---|---|---|
| 2002/0033848 | A1* | 3/2002 | Sciammarella | G06F 3/0481 715/838 |
| 2003/0227468 | A1* | 12/2003 | Takeda | G06F 17/30274 345/619 |
| 2004/0068423 | A1* | 4/2004 | Shaw | G06F 19/321 705/3 |
| 2004/0172616 | A1* | 9/2004 | Rothschiller | G06F 17/2247 717/114 |
| 2005/0134945 | A1 | 6/2005 | Gallagher | |
| 2005/0188057 | A1 | 8/2005 | Joo | |
| 2006/0212833 | A1* | 9/2006 | Gallagher | G06T 11/206 715/848 |
| 2006/0288304 | A1* | 12/2006 | Nomoto | G06F 17/30126 715/781 |
| 2007/0232885 | A1* | 10/2007 | Cook | G06F 19/321 600/407 |
| 2008/0016470 | A1* | 1/2008 | Misawa | G06F 17/30265 715/839 |
| 2008/0120571 | A1* | 5/2008 | Chang | G06F 3/0483 715/810 |
| 2009/0125842 | A1* | 5/2009 | Nakayama | G06F 3/0482 715/835 |
| 2009/0132588 | A1 | 5/2009 | Mahesh et al. | |
| 2010/0074590 | A1* | 3/2010 | Momosaki | G11B 27/034 386/278 |
| 2010/0205566 | A1* | 8/2010 | Matoba | G06F 3/0488 715/838 |
| 2011/0126148 | A1 | 5/2011 | Krishnaraj et al. | |
| 2011/0246942 | A1* | 10/2011 | Misawa | G06F 3/04815 715/830 |
| 2013/0033519 | A1* | 2/2013 | Sato | G06F 3/0482 345/619 |
| 2015/0220248 | A1* | 8/2015 | Ording | G06F 3/0481 715/835 |

FOREIGN PATENT DOCUMENTS

| | | |
|---|---|---|
| JP | 2005107723 A | 4/2005 |
| JP | 2006006915 A | 1/2006 |
| JP | 2008250750 A | 10/2008 |
| JP | 2010182018 A | 8/2010 |
| WO | 2011122401 A1 | 10/2011 |

OTHER PUBLICATIONS

International Search Report and Written Opinion dated Apr. 11, 2014 which was issued in connection with PCT Patent Application No. PCT/US2014/012991 which was filed on Jan. 24, 2013.

\* cited by examiner

| Conference | 2012 | February | × × × × × × — $C_{UID}$ |
| | | | × × × × × × — $C_{UID}$ |
| | | | × × × × × × — $C_{UID}$ |

| Conference | 2012 | February | × × × × × × ~ $C_{UID}$ |
| | | | × × × × × × ~ $C_{UID}$ |
| | | | × × × × × × ~ $C_{UID}$ |
| | | June | × × × × × × ~ $C_{UID}$ |
| | | | × × × × × × ~ $C_{UID}$ |
| | | | × × × × × × ~ $C_{UID}$ |
| | | | × × × × × × ~ $C_{UID}$ |

DISPLAY DEVICE AND IMAGE DISPLAY SYSTEM

CROSS-REFERENCE TO RELATED APPLICATIONS

This is a national stage application under 35 U.S.C. § 371(c) of prior filed, co-pending PCT application serial number PCT/US2014/012991, filed on Jan. 24, 2014, which claims priority to Japanese Patent Application Serial No. 2013-014405, filed on Jan. 29, 2013 and titled DISPLAY DEVICE AND IMAGE DISPLAY SYSTEM. The above-listed applications are herein incorporated by reference.

TECHNICAL FIELD

The present invention relates to a display device that displays a list of images based on data containing associated information on multiple attributes as metadata, and an image display system.

BACKGROUND

Japanese Patent Application Number 2010-182018 describes, for example, a display device connected to a server via a network to display images based on medical data stored in the server.

The medical data stored in the server is, for example, medical image data including X-ray CT images obtained by an X-ray CT (Computed Tomography) scanner and MRI images obtained by an MRI (Magnetic Resonance Imaging) machine. Additionally, the medical data includes data obtained by scanning paper documents, e.g., medical information documents used in hospitals.

SUMMARY OF THE INVENTION

In some cases, quite a number of medical images and documents are prepared for hospital patients and are stored as data. An operator who makes a diagnosis of a patient needs to find associated medical images and documents depending on the purpose of use. The operator may need to keep a history of creation of medical data on a patient. Thus, the present inventor has proposed a display device that displays a list of medical images and documents in a matrix in response to these needs.

The list will be specifically described below. The uppermost row and the leftmost column of the list are the display fields of associated information. Furthermore, a cell specified by the associated information displayed on the two display fields of the associated information contains a corresponding image. For example, thumbnails of medical images and documents on the same date are displayed in a row direction (horizontal direction) while thumbnails of the same document type are displayed in a column direction (vertical direction).

For example, in the case of thumbnails of the same document type (the same associated information) on the same date, all the thumbnails cannot be fully listed. Hence, the present inventor has examined a window displaying all the thumbnails of the cells on the list while each of the cells displays only one representative thumbnail. In addition to the window containing thumbnails of common associated information, the present inventor has examined a window displaying thumbnails of common information other than the associated information on the list. Thus, more thumbnails can be displayed on the window in addition to the list without switching screens on the displayed list.

However, the display of windows of different types is confusing to an operator.

An aspect of the invention devised to solve the problem has a list of simplified images based on data containing associated information of multiple attributes as metadata. A display is provided to display the list in a matrix in which the simplified images are located for respective pieces of associated information of one attribute in a row direction while the simplified images are located for respective pieces of associated information of another attribute in a column direction. The display has a first window and a second window that are displayed in different display modes on the list, the first window containing the images sharing the associated information of one attribute and the associated information of another attribute in the list of the images, the second window containing the images associated from a different point of view from the metadata in the list of images.

The invention according to the aspect displays the first window and the second window in different display modes, thereby easily distinguishing between the first window and the second window.

BRIEF DESCRIPTION OF THE DRAWINGS

FIG. 7 shows an example of a table.

FIG. 13 shows the table including UIDs in the UID fields of the "June" folder.

DETAILED DESCRIPTION

Figure 1:
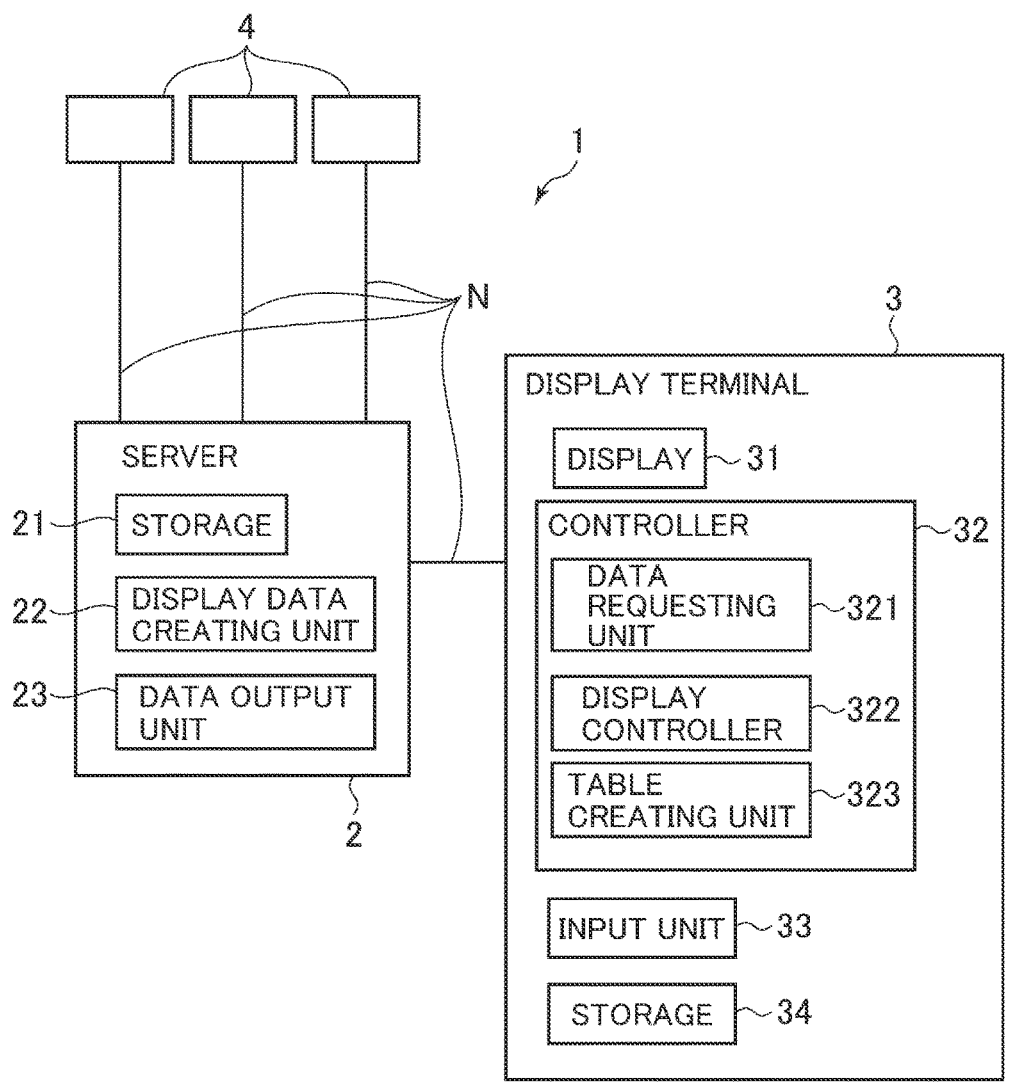
FIG. 1 is a block diagram illustrating an image display system according to an embodiment.

An embodiment of the present invention will be specifically described below with reference to the accompanying drawings. An image display system 1 in FIG. 1 includes a server 2 and a display terminal 3 that are connected to each other via a network N. The image display system 1 is a system for displaying images related to medical. The server 2 is connected to multiple department systems 4 via the network N. The image display system 1 is an exemplary embodiment of the image display system according to the present invention. The display terminal 3 is an exemplary embodiment of a display device according to the present invention.

The server 2 includes a storage 21, a display data creating unit 22, and a data output unit 23. The storage 21 is, for example, an HDD (Hard Disk Drive). The storage 21 stores, for example, medical data inputted to the server 2 from the department systems 4 through the network N. The server 2 is an exemplary embodiment of a server according to the present invention. The storage 21 is an exemplary embodiment of a storage according to the present invention.

The medical data stored in the storage 21 is data on a patient created in medical facilities or examination facilities for conducting laboratory tests. The medical data includes medical image data, document data, and numeric data. The medical data is an exemplary embodiment of data according to the present invention.

The medical image data is obtained by, for example, the modalities of the department systems 4. The medical image data includes, for example, X-ray CT images, MRI images, and ultrasound images. The document data includes, for example, medical image interpretation reports, medical information documents, consent forms such as a surgical consent form and an examination consent form, interview sheets, application forms, and examination results. Document data includes PDF (Portable Document Format) data created by scanning paper documents. The numeric data is data on numerical values pertaining to patients and indicates, for example, examination results.

The medical data includes a log of patient's biological information such as electrocardiograms and data on other patient's records as well as the medical image data, the document data, and the numeric data.

The medical data includes metadata as well as a data body. The metadata includes associated information on multiple attributes, e.g., a patient's name, a patient's ID, a date, a document type, a document category, and a hospital department. In this case, "associated information" specifically means a name, a date, a document type, a document category, and a hospital department while the attributes indicate the attributes of the associated information. For example, associated information with an attribute "document type" includes "CT" and "MRI" and associated information with an attribute "hospital department" includes "radiology" and "cardiology". Metadata is a concept containing attribute information (e.g., information on "document type") and specific attribute information (i.e., associated information such as "CT").

The metadata further includes a Unique ID (hereinafter, will be called "UID") that is information for identifying medical data.

For example, the metadata includes data automatically provided by the department systems 4, for example, modalities such as an X-ray CT scanner and manually inputted data.

A date in the metadata is, for example, the creation date of medical data. The date in the metadata may include a year and a time as well as a day. In the case of medical image data, the creation date may be a date of imaging. In the case of document data, the creation date may be a date of document creation.

A document type in the metadata is information on a medical data type. The information indicates types of medical images of MRI (Magnetic Resonance Imaging) and US (Ultrasound) and document types such as a hospitalization consent form, a hospitalization application, a hospitalization interview sheet, an examination consent form, and a surgical consent form. A document category in the metadata is information indicating a leading concept of a document type, for example, a consent form.

A hospital department in the metadata is information indicating a department having requested creation of medical data, for example, radiology and cardiology.

An attribute in the metadata may be determined beforehand. In this case, the attribute may be deleted or an attribute may be added.

The storage 21 stores a table TA that associates a folder name with the UID of medical data on a simplified image M contained in a folder, as will be described later.

The display data creating unit 22 creates data on images displayed on the display terminal 3. For example, the display data creating unit 22 creates data on a list X of simplified images M for the same patient based on medical data stored in the storage 21. The list X is displayed on the display terminal 3 as will be described later (for example, see FIG. 2). The display data creating unit 22 is an exemplary embodiment of a list creating unit in the present invention.

Figure 6:
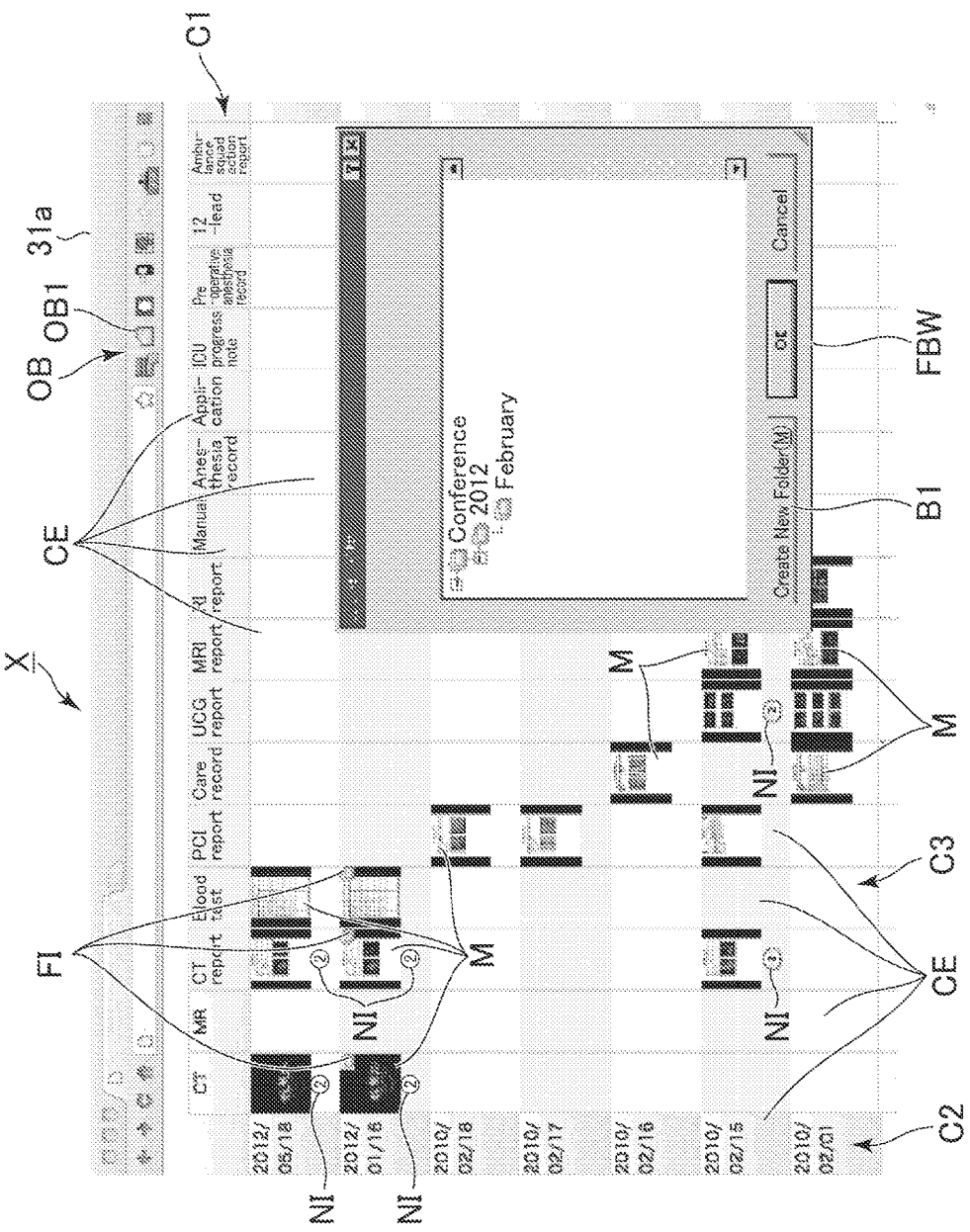
FIG. 6 shows the display screen with a displayed folder browser window.

Furthermore, the display data creating unit 22 creates data for a folder viewer FV displayed on the display terminal 3 (for example, see FIG. 6). The folder viewer FV will be discussed later.

Figure 11:
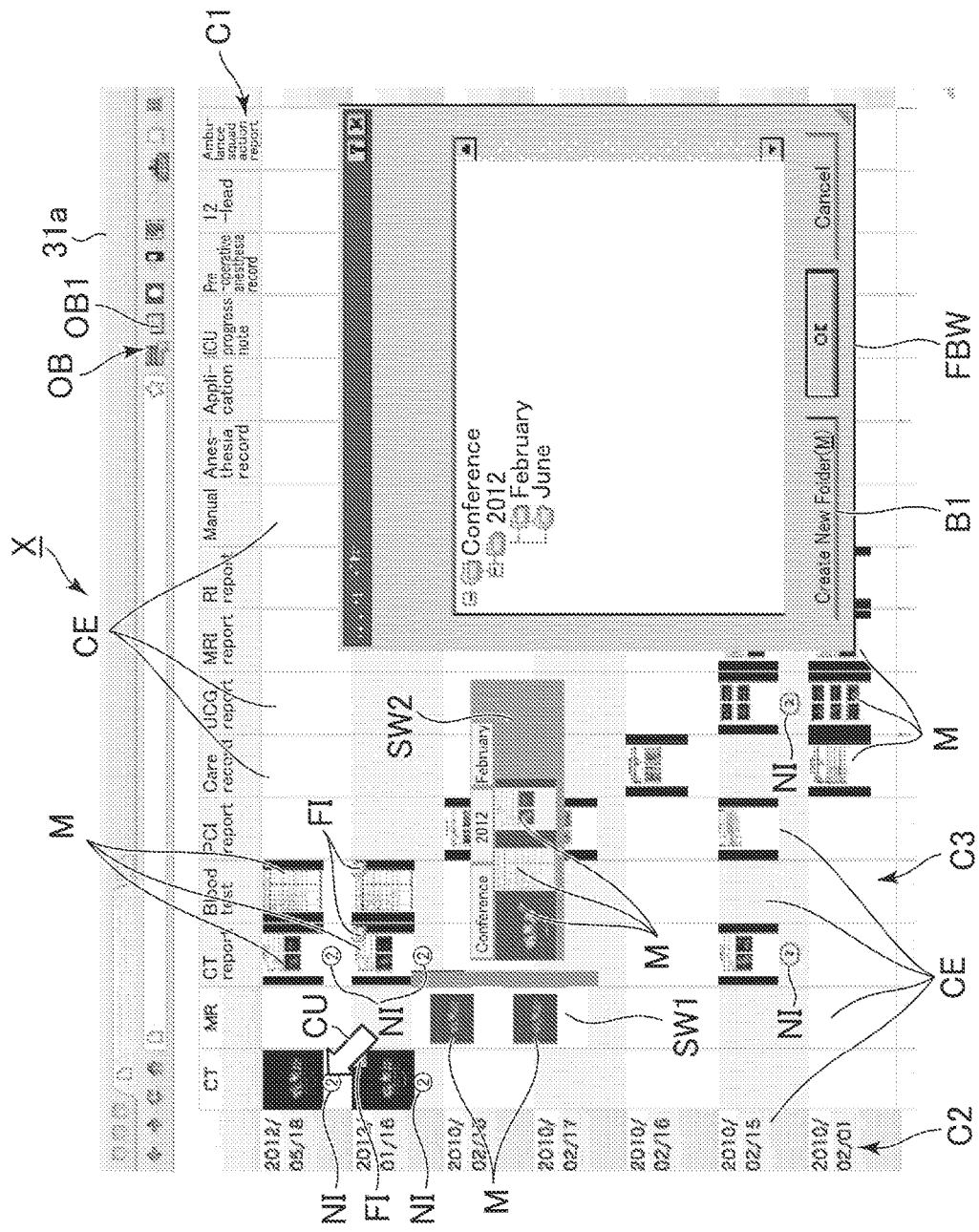
FIG. 11 shows the display screen with a displayed first sub window.

Moreover, the display data creating unit 22 creates data for a first sub window SW1 and a second sub window SW2 that are displayed on the list X (for example, see FIG. 11). The creation of data will be specifically described later.

The data output unit 23 outputs data from the server 2 to the display terminal 3 in response to a request from the display terminal 3.

In FIG. 1, the display data creating unit 22 and the data output unit 23 are provided in the same server as the storage 21 that stores the medical data. The display data creating unit 22 and the data output unit 23 may be provided in a server different from that of the storage 21.

The display terminal 3 is, for example, a general-purpose personal computer. Alternatively, the display terminal 3 may be a tablet computer. The display terminal 3 includes a display 31, a controller 32, an input unit 33, and a storage 34.

The display 31 is, for example, an LCD (Liquid Crystal Display) or a CRT (Cathode Ray Tube). The display 31 is an exemplary embodiment of a display in the present invention.

The controller 32 includes a data requesting unit 321, a display controller 322, and a table creating unit 323. The data requesting unit 321 outputs a signal for requesting data containing the list X to the server 2, in response to an operator's input on the input unit 33.

Figure 2:
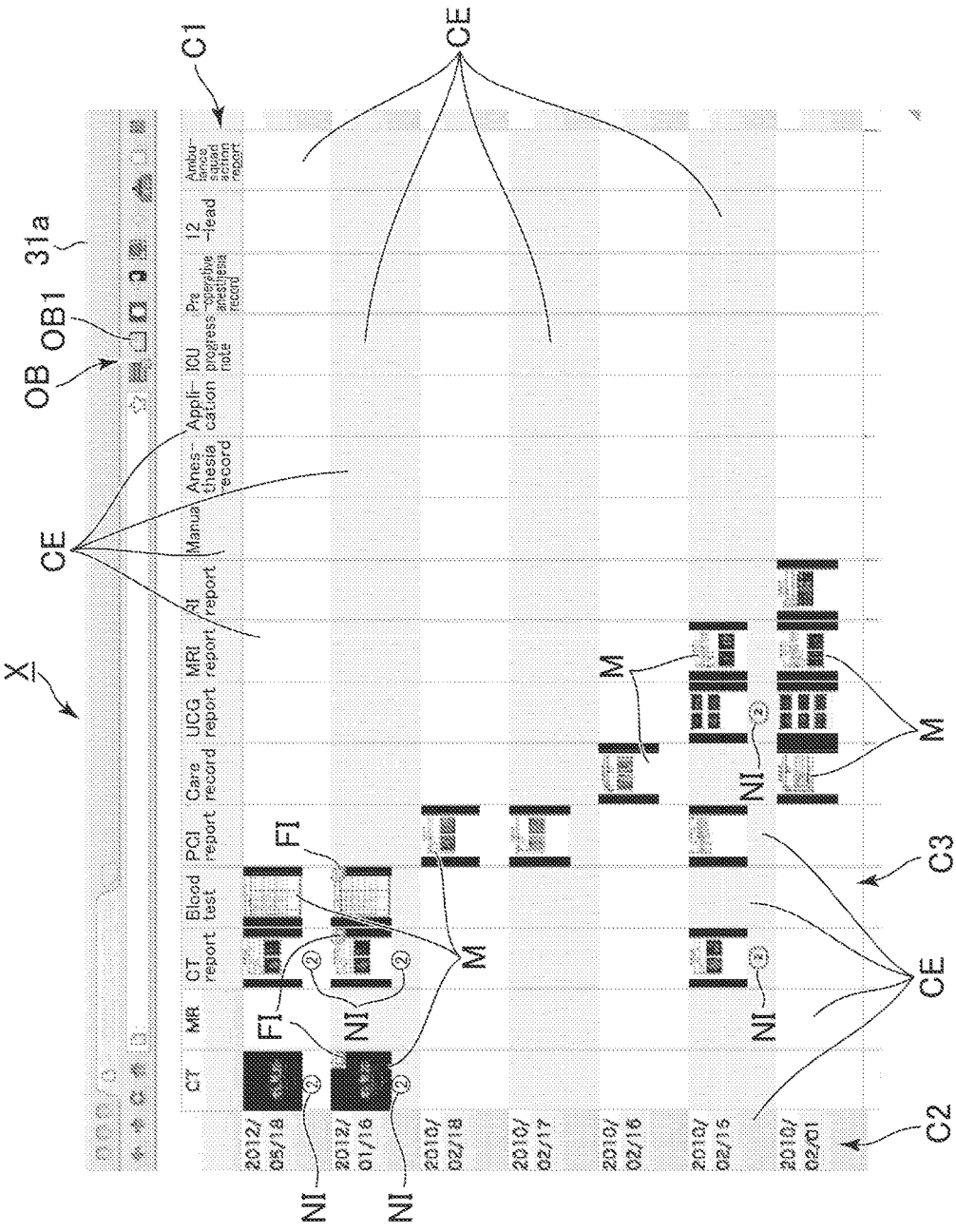
FIG. 2 shows the display screen of a display indicating a list.

The display controller 322 displays an image on a display screen 31a of the display 31. For example, as shown in FIG. 2, the display controller 322 displays the list X on the display screen 31a of the display 31 based on data in the list X inputted from the server 2. In FIG. 2, the display 31 displays a part of the list X created by the display data creating unit 22.

The list X contains associated information display columns C1 and C2 and a simplified image display column C3. The associated information display columns C1 and C2 and the simplified image display column C3 are each composed of multiple cells CE. The associated information display column C1 includes the cells CE that are disposed in a row direction (horizontal direction) so as to constitute an uppermost row in the list X. The display column C2 for associated information includes the cells CE that are disposed in a column direction (vertical direction) so as to constitute a leftmost column in the list X.

The display controller 322 displays associated information of the same attribute in the associated information display column C1. The display controller 322 also displays associated information of the same attribute in the associated information display column C2. The associated information display column C1 and the associated information display column C2 display the associated information of different attributes. In FIG. 2, a document type is displayed in the associated information display column C1 while a date (year, month, and day) is displayed in the associated information display column C2. The associated information displayed in the associated information display column C1 is an exemplary embodiment of associated information with an attribute in the present invention. The associated information displayed in the associated information display column C2 is an exemplary embodiment of associated information with another attribute in the present invention.

The attributes of the associated information display columns C1 and C2 may be changed by an operator's input with the input unit 33.

The simplified images M are displayed in the simplified image display column C3 based on medical data stored in the storage 21. The simplified images M are, for example, thumbnail images. Data on the simplified images M is created by the display data creating unit 22 of the server 2. The simplified image M is an exemplary embodiment of an image based on data in the present invention.

The creation of the image M by the display data creating unit 22 will be described below. The display data creating unit 22 converts the medical image data to a proper display size in the list X. A list of images of this size (e.g., 64×64 pixels or 96×96 pixels) can be displayed on the display screen 31a.

In the case where medical data displayed as the simplified images M is numeric data, the simplified images M created by the display data creating unit may be images indicating the contents of the numeric data. For example, an image indicating the contents of numeric data includes characters indicating the contents of the numeric data. The characters indicating the contents of the numeric data show a type of examination.

The simplified image M displayed in the simplified image display column C3 is clicked by an operator with the input unit 33, allowing the display controller 322 to display an image (original image) based on original medical data from which the clicked simplified image M has been created. The medical data is obtained from the server 2. Specifically, the data requesting unit 321 first requests the original medical data of the clicked simplified image M from the server 2. This request includes the UID of the original medical data. In the server 2, the requested medical data is read from the storage 21 based on the UID inputted from the display terminal 3, and then is outputted to the display terminal 3 by the data output unit 23.

The cells CE constituting the associated information display column C1 display associated information in the vertical direction (column direction) of the simplified image display column C3. The cells CE constituting the associated information display column C2 display associated information in the horizontal direction (row direction) of the simplified image display column C3. The simplified images M are arranged in a matrix in the simplified image display columns C3. In the simplified image display columns C3, the simplified images disposed in the column direction have associated information displayed in the cell CE constituting the associated information display column C1 while the simplified images M disposed in the row direction have associated information displayed in the cell CE constituting the associated information display column C2. In the simplified image display column C3, the cell CE specified by the associated information of the associated information display column C1 and the associated information of the associated information display column C2 contains the corresponding simplified image M.

Specifically, FIG. 2 displays the list X in which the simplified images M of respective document types are disposed in the column direction and the simplified images M on respective dates are disposed in the row direction. For example, in the simplified image display column C3, a simplified image M (a thumbnail image indicating a CT image) based on medical data having information indicating the CT image as associated information is displayed by the display controller 322 in the column of the cells CE displayed as "CT". Moreover, in the simplified image display column C3, a simplified image M based on medical data having date information of May 18, 2012 as associated information is displayed by the display controller 322 in the row of the cell CE displayed as "May 18, 2012" in, for example, the associated information display columns C2. Thus, the display controller 322 displays the list X in which the simplified images M for associated information of an attribute are disposed in the row direction and the simplified images M for associated information of another attribute are disposed in the column direction.

If multiple pieces of medical data need to be displayed in one of the cells CE in the list X, that is, if multiple pieces of medical data share two types of associated information displayed in the list X, the cell CE only displays representative one of the simplified images M. For example, in the case of multiple CT images on May 18, 2012, only representative one of the simplified images M is displayed in the cell CE of the list X. The display data creating unit 22 may, however, create two or more simplified images M.

If the attributes of the associated information display columns C1 and C2 are changed, the display data creating unit 22 creates data on the list X in which associated information of the changed attributes is displayed in the associated information display columns C1 and C2 and the simplified images are relocated according to the changed attributes.

The list X can be scrolled by dragging with the input unit 33. If the display 31 is a touch panel display, dragging or flicking with a finger of an operator can scroll the list X.

The displayed list X allows the operator to recognize the history of medical data creation of a patient at a glance. As described above, the list X satisfactorily shows medical data, allowing the operator to easily recognize the frequency of hospital visiting of a patient.

The simplified images constituting the list X include simplified images M based on medical data stored in a folder by an operator's input with the input unit 33, which will be specifically discussed later.

The table creating unit 323 creates a table TA for associating a folder name with a UID of medical data as will be described later.

The input unit 33 includes a keyboard and a mouse. The input unit 33 is an exemplary embodiment of an input unit in the present invention.

The storage 34 is, for example, a HDD or semiconductor memory such as RAM (Random Access Memory) and ROM (Read Only Memory).

The department system 4 is a hospital department system, for example, a radiology information system (RIS) including modalities such as an X-ray CT scanner and an MRI machine, and a laboratory test system.

The action of the image display system 1 of the present embodiment will be described below. According to the image display system 1 of the present embodiment, the simplified images M constituting the list X of a patent can be categorized into folders by an operator. In this example, the simplified images M used for conferences in a hospital are categorized into folders by an operator. The simplified images M are images for a patient P.

Figure 3:
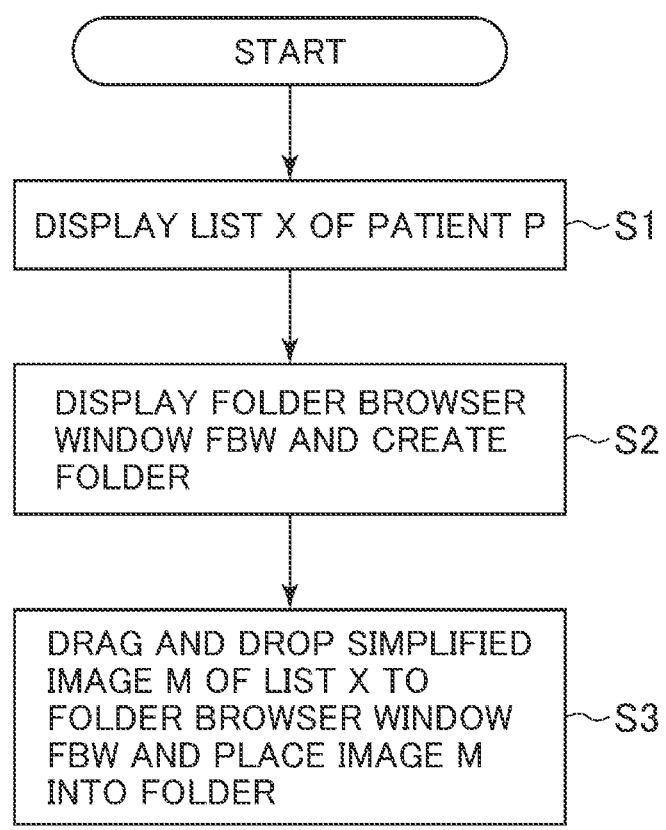
FIG. 3 is a flowchart for explaining storage of a simplified image into a folder.

Data on the simplified images M used for the conferences is placed into folders by the operator from the simplified images M constituting the list X. Specifically, the process will be discussed below with reference to the flowchart of FIG. 3. First, in step S1, the operator displays the list X on the display screen 31a. Specific processing in step S1 will be described below with reference to the flowchart of FIG. 4.

Figure 4:
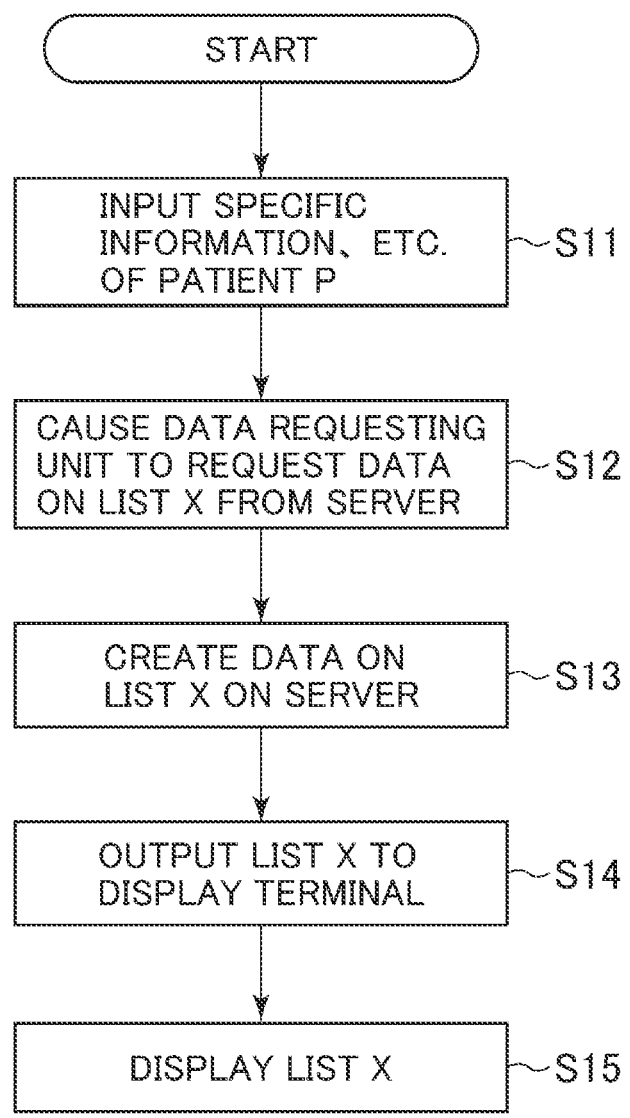
FIG. 4 is a flowchart specifically showing processing in step S1 of FIG. 3.

First, in step S11 of FIG. 4, the operator inputs an instruction for display of the list X and specific information on the patient P, for example, a name and an ID to the input unit 33 of the display terminal 3. Subsequently, in step S12, the data requesting unit 321 requests data on the list X of the patient P with the inputted specific information from the server 2. This request includes the specific information of the patient P.

In step S12, data on the list X is requested. In step S13, the display data creating unit 22 of the server 2 creates data on the list X. Specifically, the display data creating unit 22 first specifies all the pieces of medical data stored for the patient P in the storage 21 based on the specific information on the patient P from the data requesting unit 321. The multiple pieces of medical data are created for the patient P at different times. Furthermore, the display data creating unit 22 creates data on the list X of the simplified images M for the patient P, based on the medical data specified for the patient P.

Subsequently, in step S14, the data output unit 23 outputs, to the display terminal 3, data on the list X created in step S13. In step S15, the display controller 322 displays the list X on the display screen 31a based on the data on the list X inputted to the display terminal 3 (see FIG. 2). The display controller 322 displays operation buttons OB with the list X.

Figure 5:
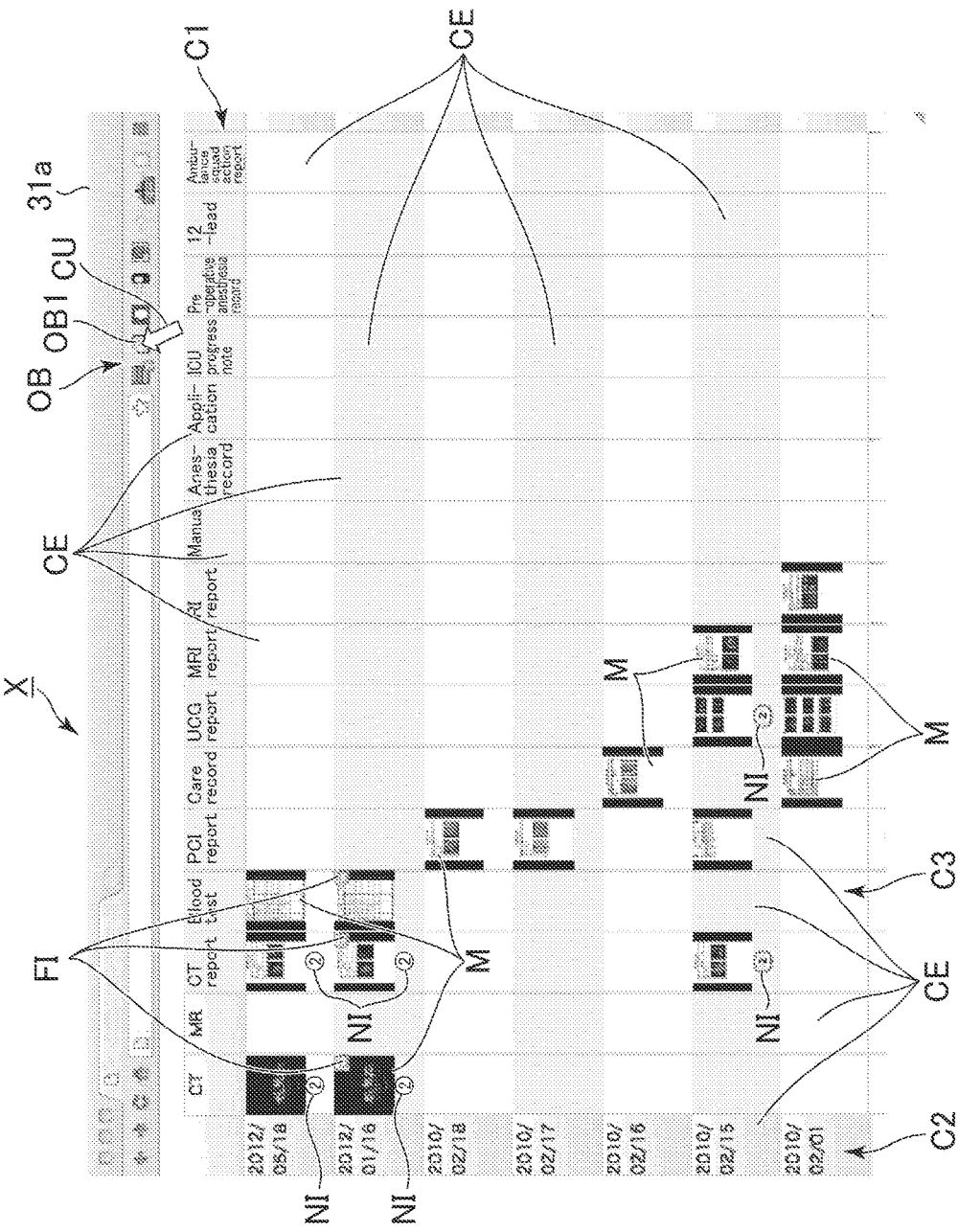
FIG. 5 shows the display screen with a clicked first operation button.

Subsequently, in step S2, the operator displays a folder browser window FBW on the display 31 and creates folders, which will be specifically described below. First, as shown in FIG. 5, the operator uses the input unit 33 so as to click on a first operation button OB1 of the operation buttons OB with a cursor CU. As shown in FIG. 6, clicking on the first operation button OB1 allows the display controller 322 to display the folder browser window FBW on the display screen 31a. FIG. 6 shows the folder browser window FBW that displays a folder "conference-2012-February".

The display of the folder browser window FBW will be discussed below. A click on the first operation button OB1 first allows the data requesting unit 321 to request data of the folder browser window FBW from the server 2. Subsequently, the display data creating unit 22 of the server 2 creates data on the folder browser window FBW with reference to the table TA stored in the storage 21. When the data on the folder browser window FBW is outputted to the display terminal 3 from the data output unit 23, the display controller 322 displays the folder browser window FBW based on the data.

The table TA will be discussed below. The table TA includes a "conference" folder that has a "2012" folder containing a "February" folder. In the present embodiment, these folders constitute a hierarchical structure. The "February" folder contains the simplified images M used in conferences in February 2012. Thus, as shown in FIG. 7, the storage 21 stores the table TA that associates a folder name "conference-2012-February" with the UID of medical data stored in the folder. The table TA in FIG. 7 has a UID field of $C_{UID}$ that indicates the UID of medical data of the simplified images M contained in the "February" folder ("x" marks in FIG. 7).

The table TA is not limited to a specific patient. Hence, the folder may contain the simplified images of patients other than the patient P.

Figure 8:
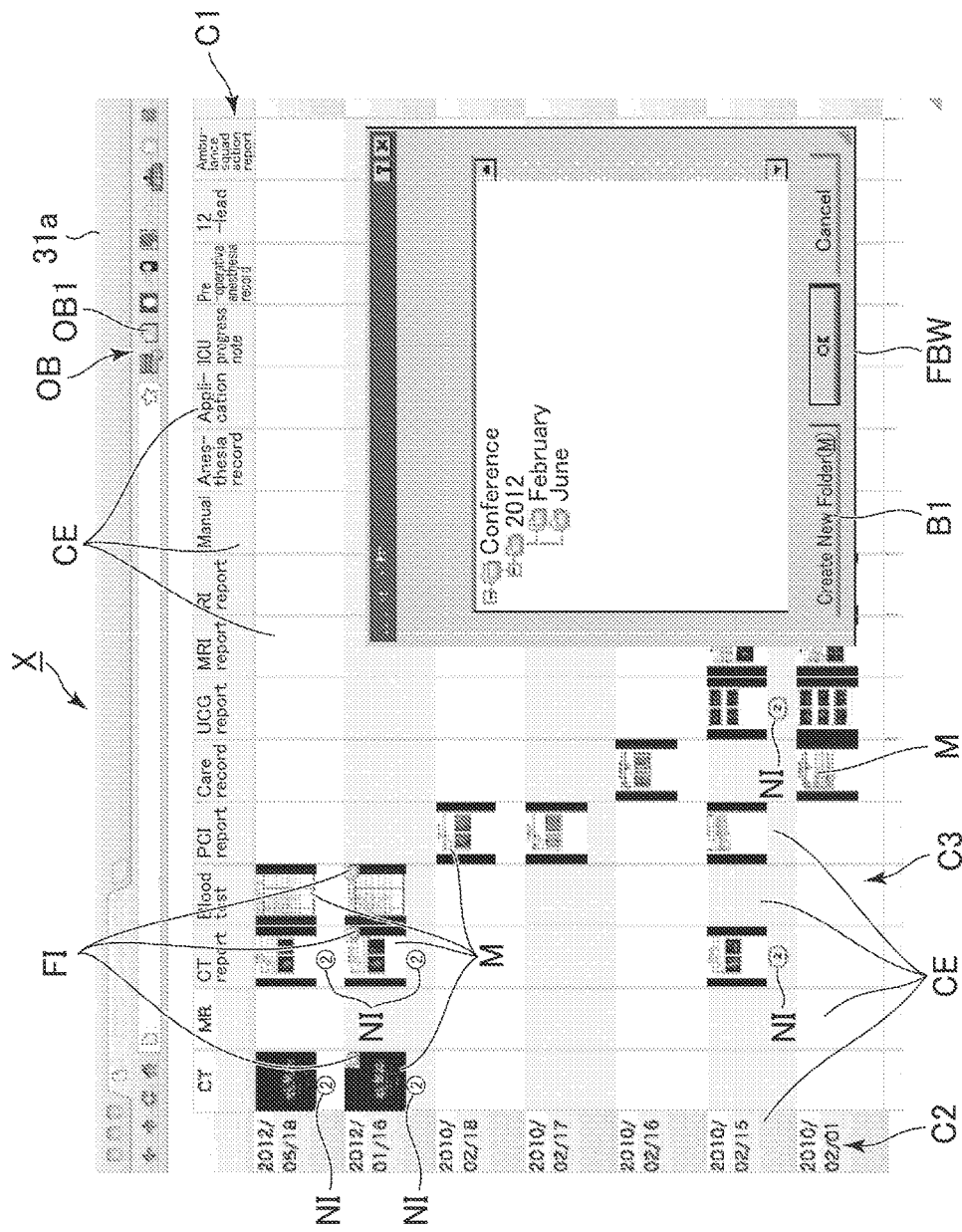
FIG. 8 shows the display screen with the folder browser window displayed with a new "June" folder.

When the folder browser window FBW is displayed, the operator uses the input unit 33 so as to click a "create new folder" button B1 with the cursor CU (not shown in FIG. 6), thereby creating a new folder. In this case, simplified images M used in conferences in "June" are placed into a folder by the operator. As shown in FIG. 8, a "June" folder is created as a new folder.

Figure 9:
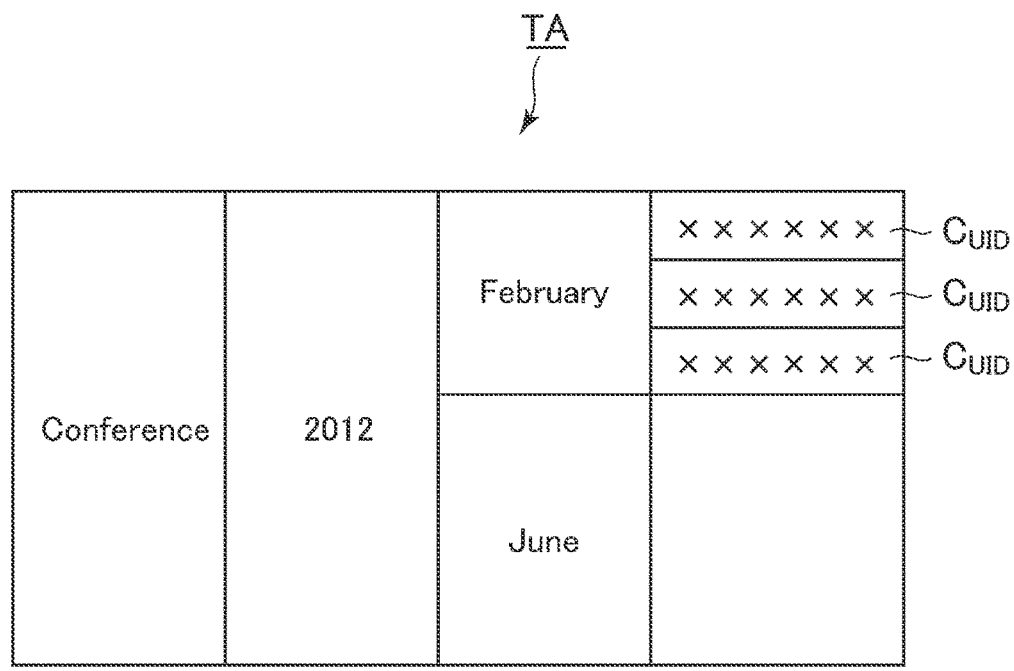
FIG. 9 shows the table with the added "June" folder.

After the "June" folder is created, as shown in FIG. 9, the table creating unit 323 adds "June" to the table TA that associates folder names with the UIDs of medical data. The table TA with additional "June" is stored in the storage 34.

Figure 10:
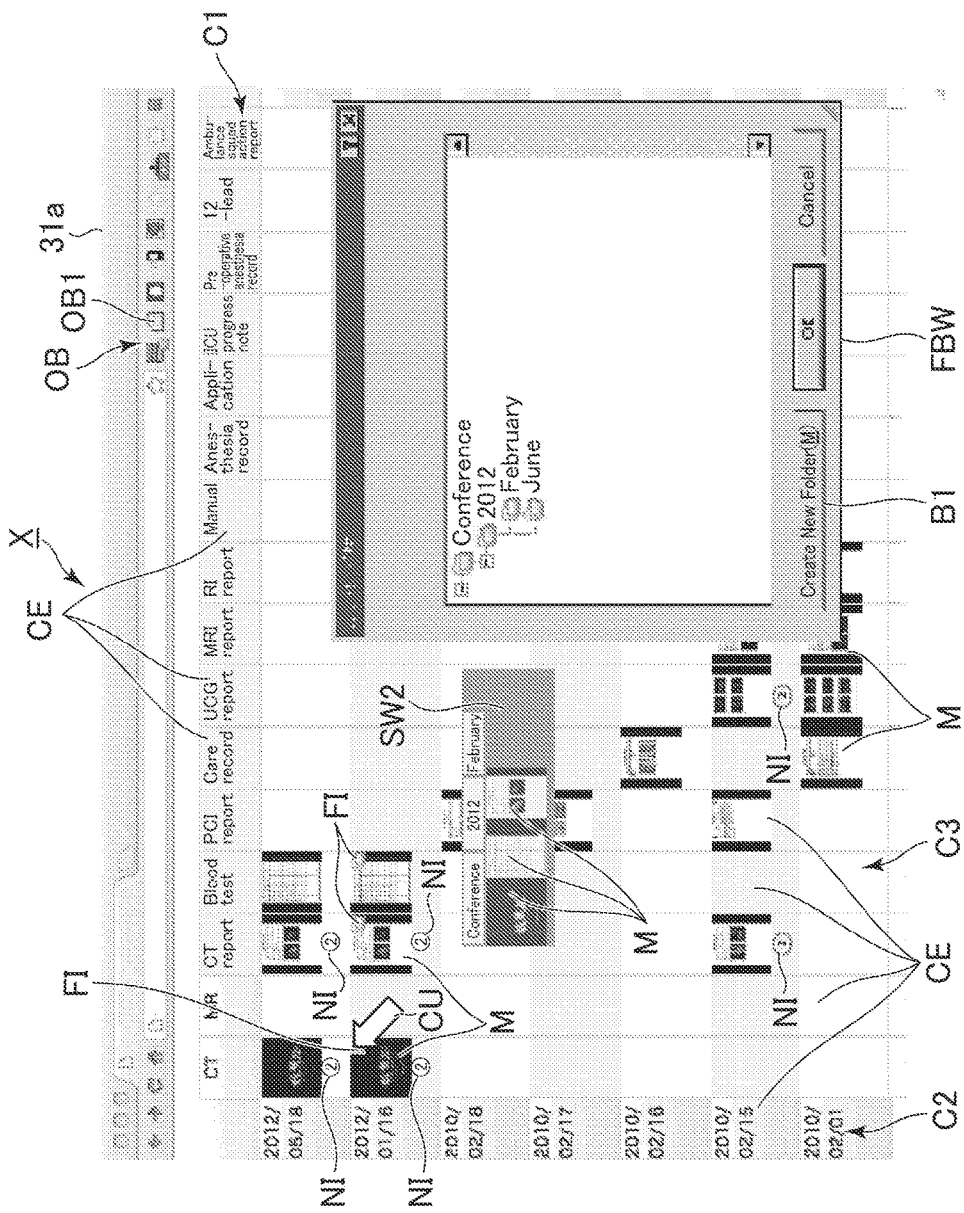
FIG. 10 shows the display screen with a displayed second sub window.

Subsequently, in step S3, the simplified images M used in conferences in June are placed into the "June" folder of the folder browser window FBW. It is assumed that the operator will also place CT images used in conferences in February into the "June" folder. If the operator confirms the simplified images M used in conferences in February before placing desired simplified images M into the "June" folder, as shown in FIG. 10, the operator clicks on a folder icon FI with the cursor CU to display a second sub window SW2. The second sub window SW2 overlies the list X. The simplified images M in the "conference-2012-February" folder are displayed in the second sub window SW2. This allows the operator to easily confirm the simplified images M used in conferences in February. The second sub window SW2 is a window containing the simplified images M in the same folder and serves as an exemplary embodiment of a second window in the present invention. Moreover, the simplified images M placed in the same folder and displayed in the second sub window SW2 serve as an exemplary embodiment of an image associated from a different point of view from metadata in a list of images.

Images based on the original medical data of the simplified images M may be displayed by clicking the simplified images M in the second sub window SW2.

The second sub window SW2 displays the folder name "conference-2012-February" of the folder containing the simplified images M used in conferences in February. Thus, the operator can easily recognize that the second sub window SW2 shows the contents of the "conference-2012-February" folder.

The second sub window SW2 is a rectangle displayed on the list X with its length extending in a horizontal direction (row direction). Specifically, the second sub window SW2 is a horizontally oriented rectangle, that is, the second sub window SW2 is shaped in one direction (horizontal direction). The simplified images M are horizontally oriented in the second sub window SW2.

The display of the second sub window SW2 will be discussed below. The simplified images M categorized in the folders have the folder icons FI. A click on the folder icon FI displays the second sub window SW2. Thus, the folder icons FI are displayed for the simplified images M displayed in the second sub window SW2. The folder icon FI is an indicator of the folder containing medical data on the simplified images M displayed with the folder icons FI. In other words, the folder icon FI is an indicator that can distinguish the simplified images based on medical data contained in the folder from the simplified images M not contained in the folder, among the simplified images M of the list X. The folder icon FI is an exemplary embodiment of an indicator and a second indicator in the present invention.

In step S13, the folder icon FI is added in the creation of data in the list X. Specifically, the display data creating unit 22 adds the folder icon FI to the corresponding simplified image M with reference to a UID contained in the table TA. In this case, in step S14, data on the list X with the folder icons FI is outputted to the display terminal 3.

When the folder icon FI is clicked, the display screen 31a displays the second sub window SW2 containing the simplified images M of data in the folder corresponding to the folder icon FI. For example, in FIG. 10, the folder icon FI displayed on the simplified image M of a CT image on Jan. 16, 2012 is clicked by the cursor CU. Data on the CT image on Jan. 16, 2012 is placed in the "February" folder. The second sub window SW2 allows the operator to confirm that a CT image used in a conference of February is an image on Jan. 16, 2012.

The folder icon FI and the simplified image are linked with folder specific information for specifying a folder (folder name). When the folder icon FI is clicked, the requesting unit 321 outputs the folder specific information to the server 2. The display data creating unit 22 of the server 2 creates data on the second sub window SW2 with reference to the folder specific information inputted from the display terminal 3. Specifically, the display data creating unit 22 specifies the UIDs of the simplified images M in the folder specified by the folder specific information, with reference to the table TA. The display data creating unit 22 then creates data on the second sub window SW2 containing the simplified images M. The data on the second sub window SW2 is outputted to the display terminal 3 by the data output unit 23. The display controller 322 displays the list X containing the second sub window SW2, based on data inputted from the server 2.

The operator confirms the simplified images M used in a conference in February, and then places the simplified images M used in a conference in June into the "June" folder along with the simplified images M of CT images used in the conference in February. Specifically, as shown in FIG. 11, the operator first displays the first sub window SW1 by clicking a numeric icon NI displayed on the cell CE. The first sub window SW1 overlies the list X. The first sub window SW1 is an exemplary embodiment of a first window in the present invention.

The numeric icon NI indicates the number of simplified images M in the cell CE having the numeric icon NI. If the single cell CE contains multiple simplified images M, only one of the simplified images M is displayed. The simplified images M share two types of associated information (in this case, a document type and a date) in the display columns C1 and C2 of the associated information in the list X. In the cell CE containing only one of the simplified images M, the numeric icon NI is not displayed.

In step S13, the numeric icon NI is added when data on the list X is created. Specifically, the display data creating unit 22 adds the numeric icon NI based on the number of specified images M created for the cell CE. In step S14, data on the list X with the numeric icon NI is outputted to the display terminal 3. The numeric icon NI is an exemplary embodiment of a first indicator in the present invention.

The first sub window SW1 displays the simplified images M in the single cell CE. When the numeric icon NI is clicked, the display data creating unit 22 of the server 2 creates data on the first sub window SW1 containing the simplified images M having two types of associated information in the cell CE with the displayed numeric icon NI. The data on the first sub window SW1 is outputted to the display terminal 3 by the data output unit 23, and then the display controller 322 displays the first sub window SW1.

In FIG. 11, since the numeric icon NI on the cell CE showing the simplified image M of a CT image on May 18, 2012 is clicked, the simplified image M of the CT image on May 18, 2012 is being displayed in the first sub window SW1. Thus, the first sub window SW1 displays the simplified images M that share types of associated information in the associated information display columns C1 and C2. The numeric icon NI is displayed for the simplified image M that is displayed in the first sub window SW1.

The first sub window SW1 is a rectangle displayed on the list X with its length extending in a vertical direction (column direction). Specifically, the first sub window SW1 is a vertically oriented rectangle, that is, the first sub window SW1 is shaped in one direction (vertical direction). The simplified images M are vertically oriented in the first sub window SW1. Thus, the first sub window SW1 and the second sub window SW2 are displayed in different directions and different display modes.

Figure 12:
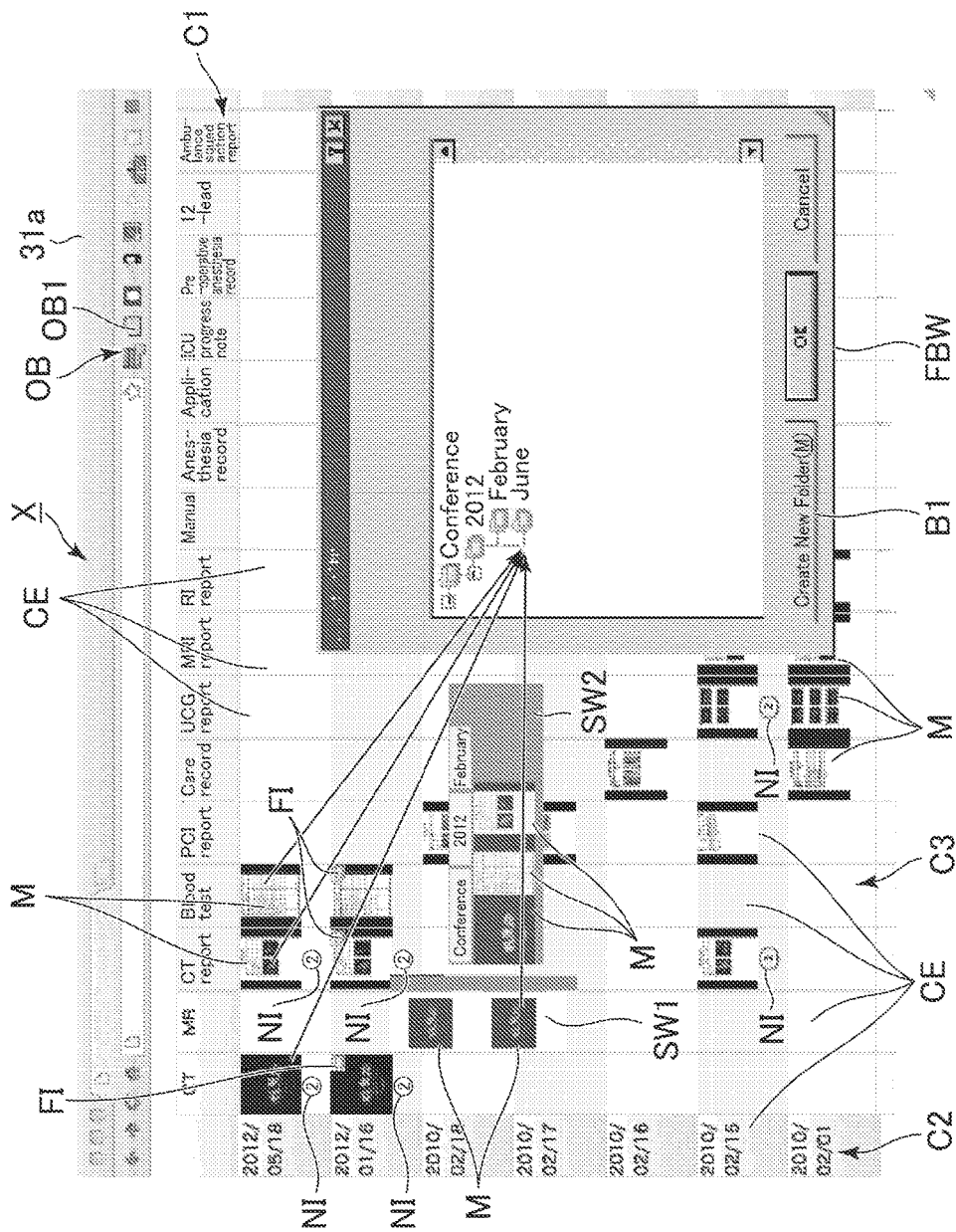
FIG. 12 is an explanatory drawing of an operation for placing simplified images for a conference in June into the "June" folder.

As shown in FIG. 12, the simplified image M to be placed into the "June folder" is dragged and dropped into the "June" folder of the folder browser window FBW by the operator. In this case, the simplified image M of a CT image on Jan. 16, 2012, a CT image on May 18, 2012, a CT report, and the simplified image M of a blood test are dragged and dropped into the "June" folder with the input unit 33. The simplified images M dragged and dropped into the folder are associated from a different point of view from metadata. The dragging and dropping of the simplified images M into the folder is an example of input for associating the images from a different point of view from metadata.

In the present embodiment, an image not displayed on the list X is placed into the "June" folder as the simplified image M of the CT image on Jan. 16, 2012. The operator selects desired one of the simplified images M displayed on the first sub window SW1 and then drags and drops the image into the "June" folder.

As described above, the operator can easily place desired one of the simplified images M into the folder only by dragging and dropping the image into the folder browser window FBW displayed on the list X.

Furthermore, the simplified image M of an image used in a conference in February can be confirmed on the first sub window SW1 while the simplified image M to be placed into the "June" folder is displayed on the first sub window SW1. Since the first sub window SW1 and the second sub window SW2 are simultaneously displayed in different directions, the windows can be easily distinguished from each other.

Dragging and dropping of the simplified image M into the folder allows the table creating unit 323 to create a table for associating a folder name with the UID of medical data. The table creating unit 323 writes, as shown in FIG. 13, the UID of medical data on the simplified image M in the "June" folder into $C_{UID}$ of the UID field in the "June" folder of the table TA. This completes the table TA (constructs a hierarchical structure) for associating the "June" folder with the UID of medical data on the simplified image M in the "June" folder. The table TA is stored in the storage 34. The table TA is outputted to the server 2, and then the table TA for the patient P in the storage 21 is updated.

When a UID is written into $C_{UID}$ of the UID field of the table TA, data on the simplified image M is placed into the folder.

Figure 14:
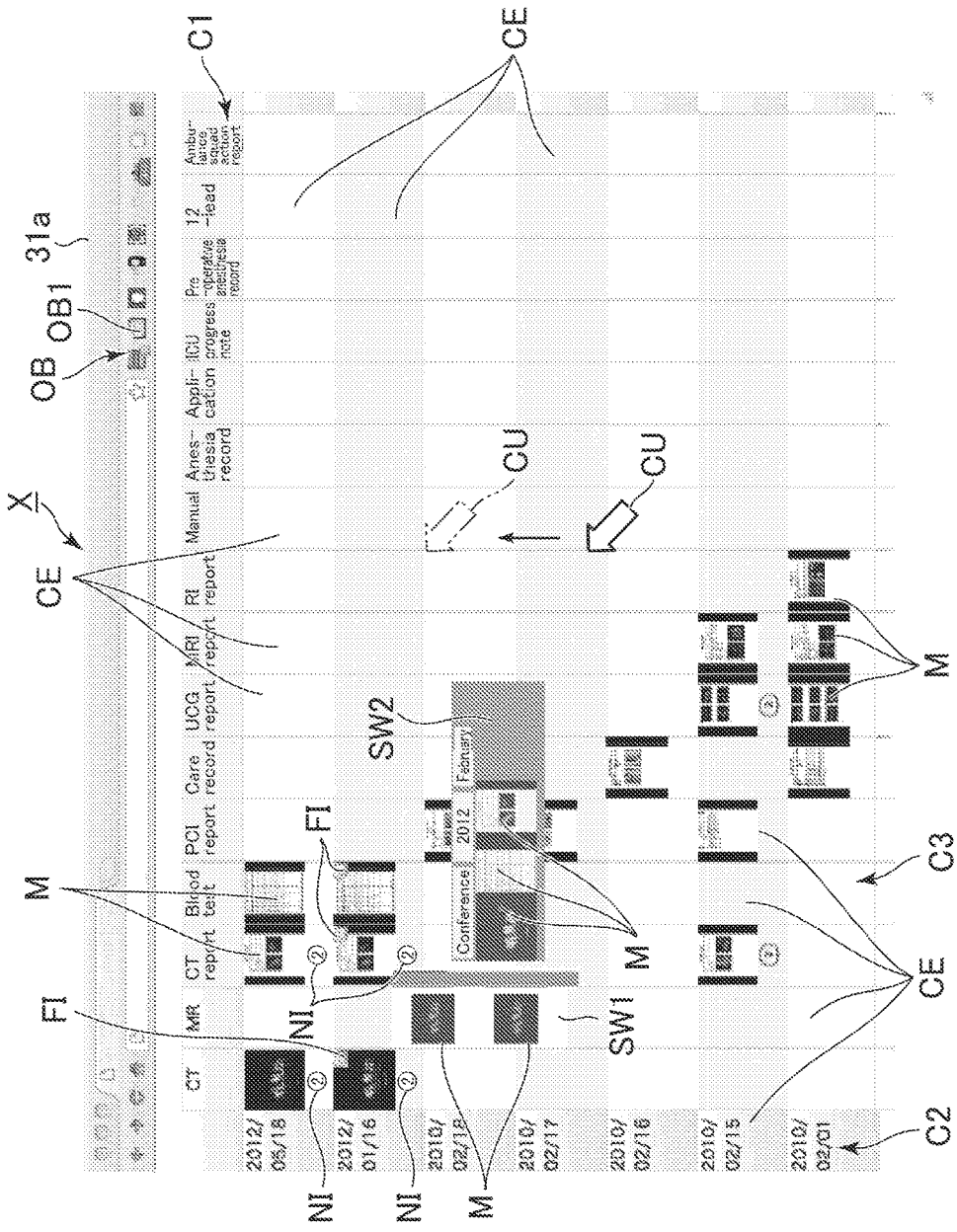
FIG. 14 is an explanatory drawing of a movement of the list.

In this way, the preparation of a conference is completed. The display screen 31a displays a part of data on the list X created by the display data creating unit 22. An input on the input unit 33 allows the operator to move a part to be displayed on the display screen 31a from the list X created by the display data creating unit 22. In other words, the operator can move the list X displayed on the display screen 31a. As shown in FIG. 14, the operator can move a displayed part of the list X by dragging the cursor CU on the list X. The dragging operation can move a displayed part of the list X in vertical, horizontal, and diagonal directions.

Figure 15:
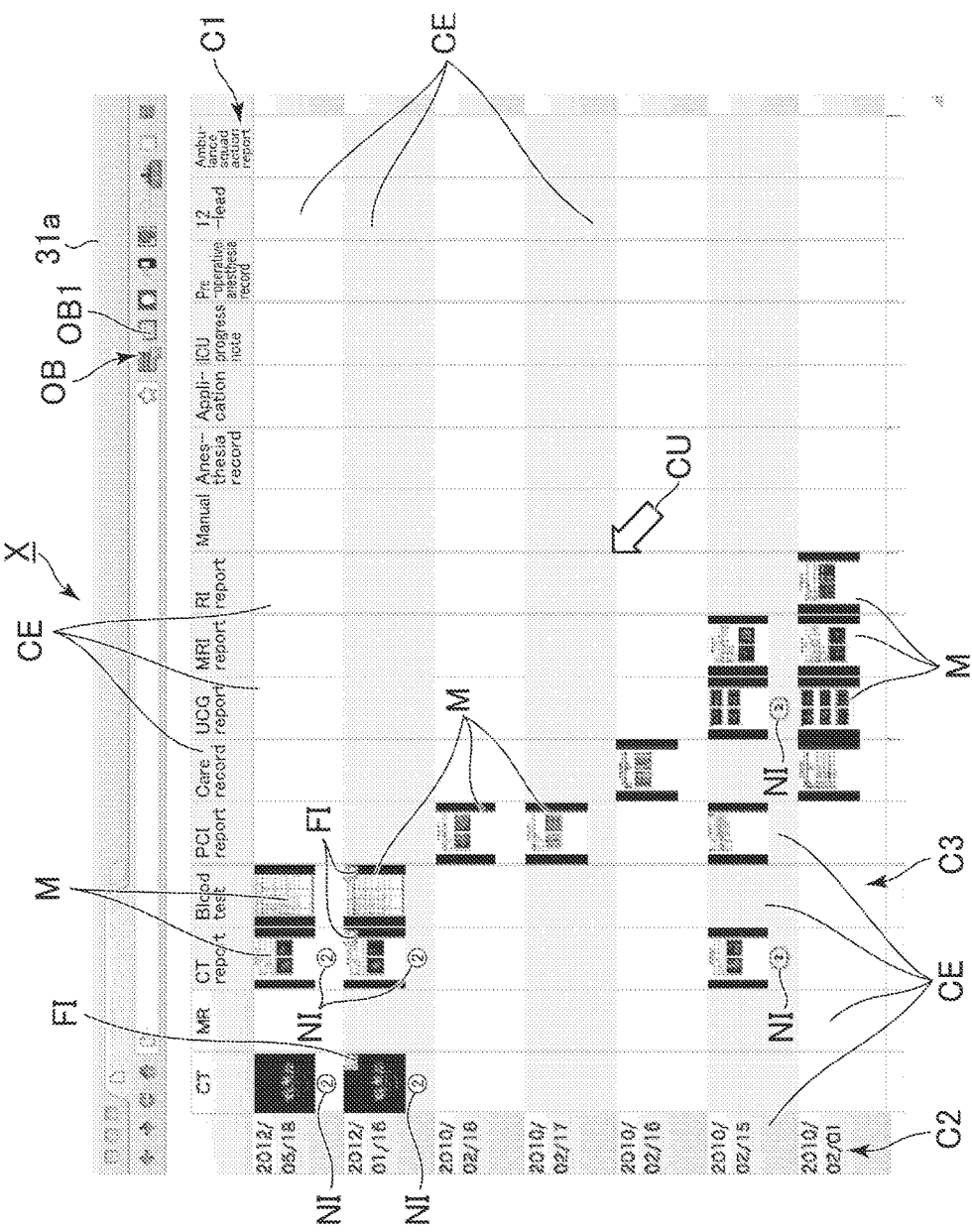
FIG. 15 shows the display screen on which the first sub window and the second sub window are hidden.

When an input (dragging) on the input unit 33 by the operator moves the list X, as shown in FIG. 15, the display controller 322 hides the first sub window SW1 and the second sub window SW2. Specifically, a press on a button of the mouse of the input unit 33 hides the first sub window SW1 and the second sub window SW2.

The first sub window SW1 and the second sub window SW2 may be hidden by clicking on the cursor CU on the list X.

For example, if the operator needs to view the simplified image M overlying the first sub window SW1 and the second sub window SW2 or move the list X to display the simplified image M hidden on the display screen 31a, the operator needs to hide the first sub window SW1 and the second sub window SW2. If the first sub window SW1 and the second sub window SW2 interfere with an operator's view or the operator does not need to display the windows, an input such as dragging and clicking on the list by the operator hides the first sub window SW1 and the second sub window SW2, achieving a simple operation.

Figure 16:
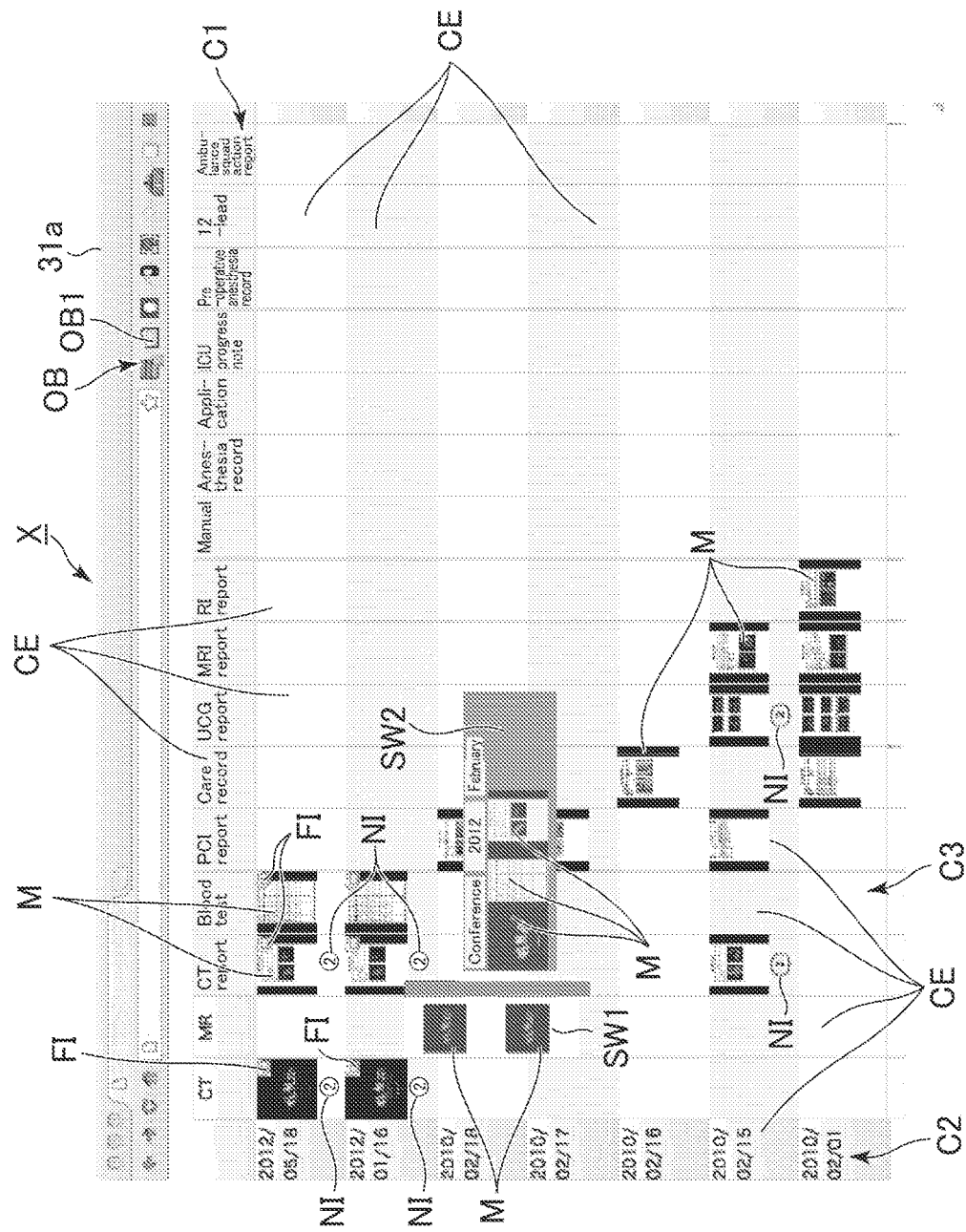
FIG. 16 shows the display screen on which folder icons are displayed on simplified images M newly placed in the folder.
Figure 17:
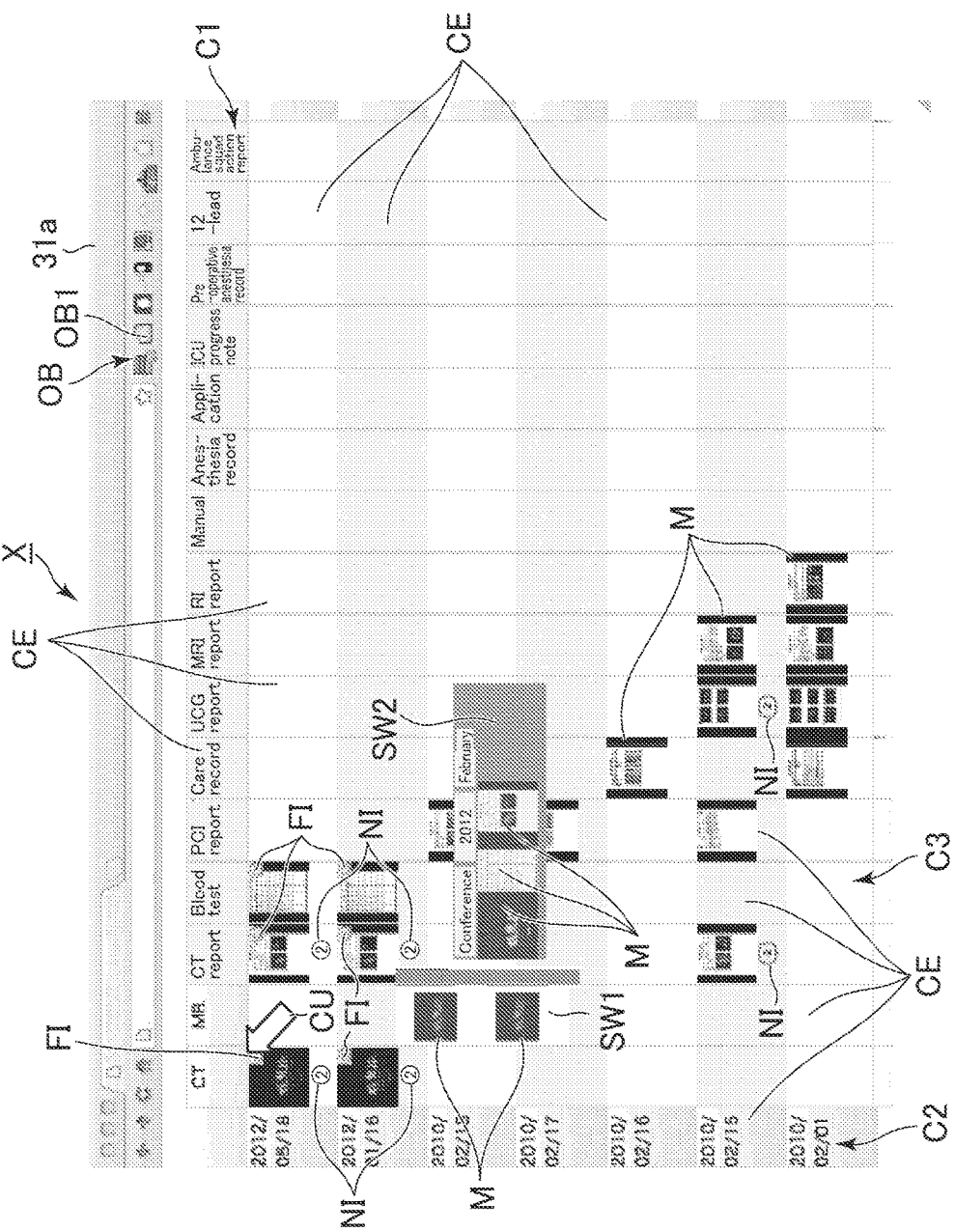
FIG. 17 shows the display screen with a cursor placed on the folder icon in the simplified image newly placed in the folder.
Figure 18:
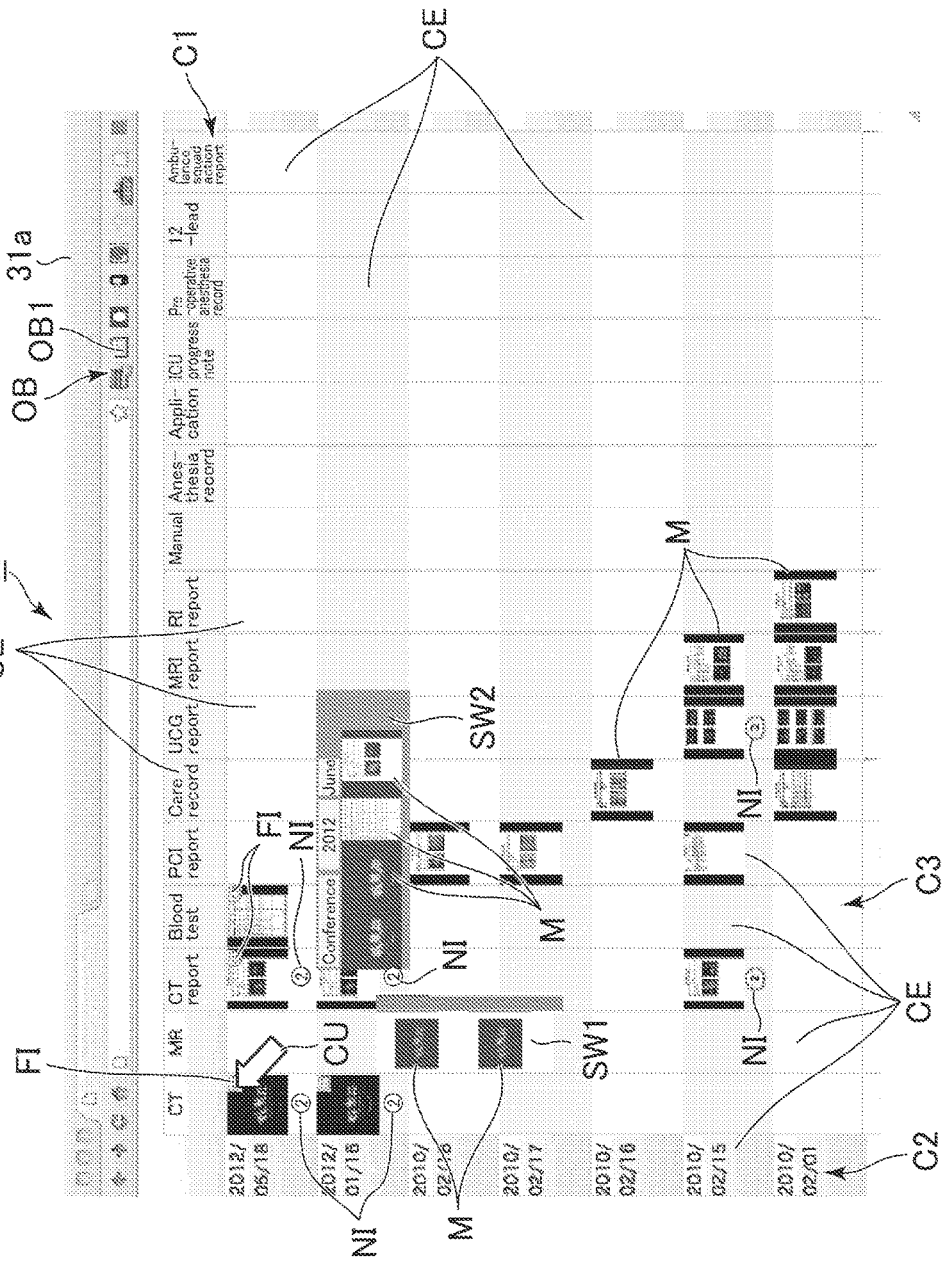
FIG. 18 shows the display screen with another second sub window.

As shown in FIG. 16, the simplified image M in the "June" folder has another folder icon FI. As shown in FIG. 17, the operator places the cursor CU to click on the folder icon FI displayed on the simplified image M (in FIG. 17, the simplified image M of a CT image on May 18, 2012) in the "June" folder. As shown in FIG. 18, this can display the second sub window SW2 containing the simplified images M placed in the "June" folder. The second sub window SW2 containing the simplified images M placed in the "June" folder is displayed instead of the second sub window SW2 containing the simplified images M placed in the "February" folder.

Figure 19:
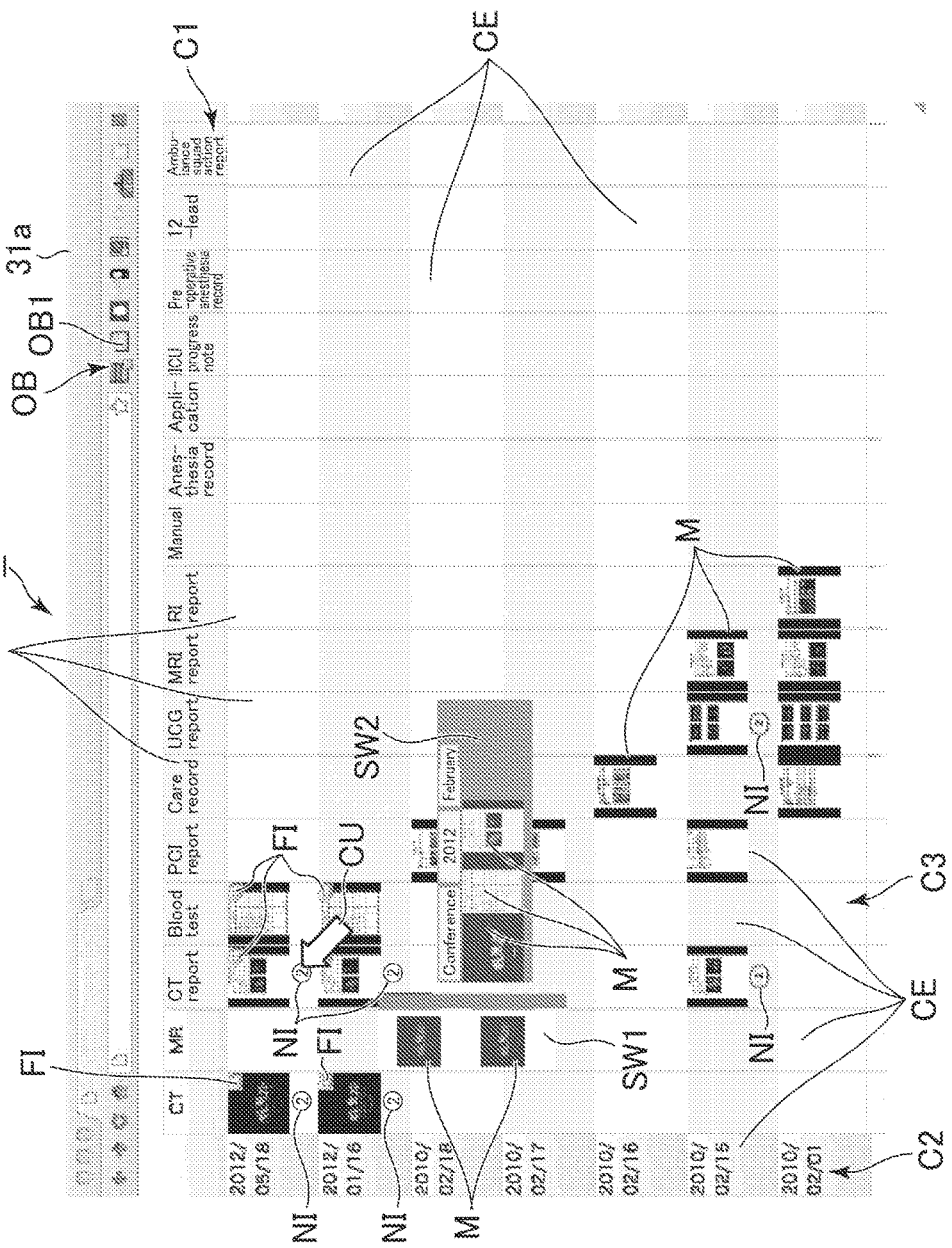
FIG. 19 shows the display screen that displays the first sub window containing the simplified images of CT images on May 18, 2012.
Figure 20:
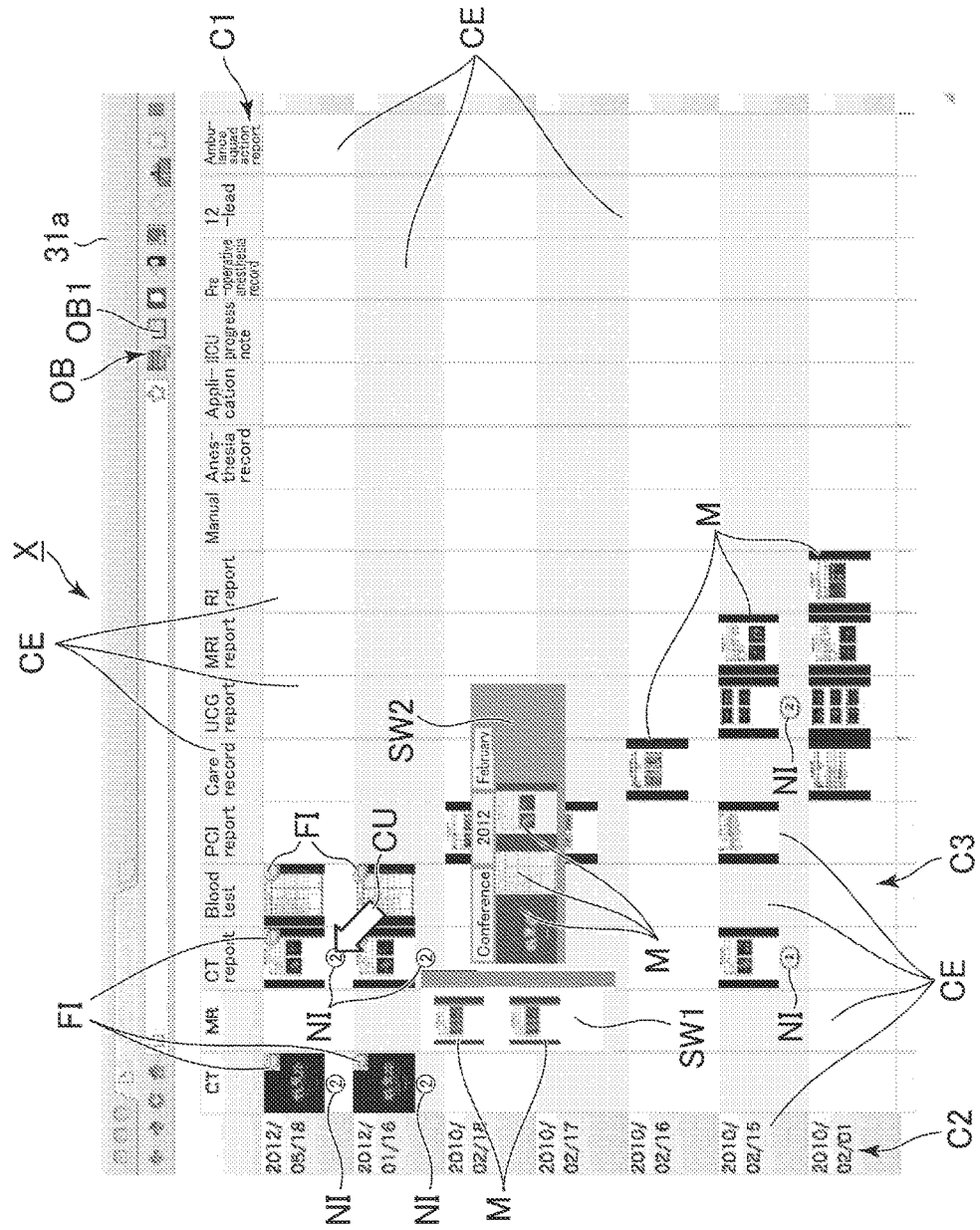
FIG. 20 shows the display screen that displays the first sub window containing the simplified images M of a CT report on May 18, 2012 instead of the simplified images of CT images on May 18, 2012.

As shown in FIG. 19, the first sub window SW1 containing the simplified images M of CT images on May 18, 2012 is displayed. In this state, as shown in FIG. 12, a click on the numeric icon NI displayed in the cell CE of a CT report on May 18, 2012 allows the first sub window SW1 containing the simplified images M of a CT report to replace the first sub window SW1 containing the simplified images M of CT images.

Figure 21:
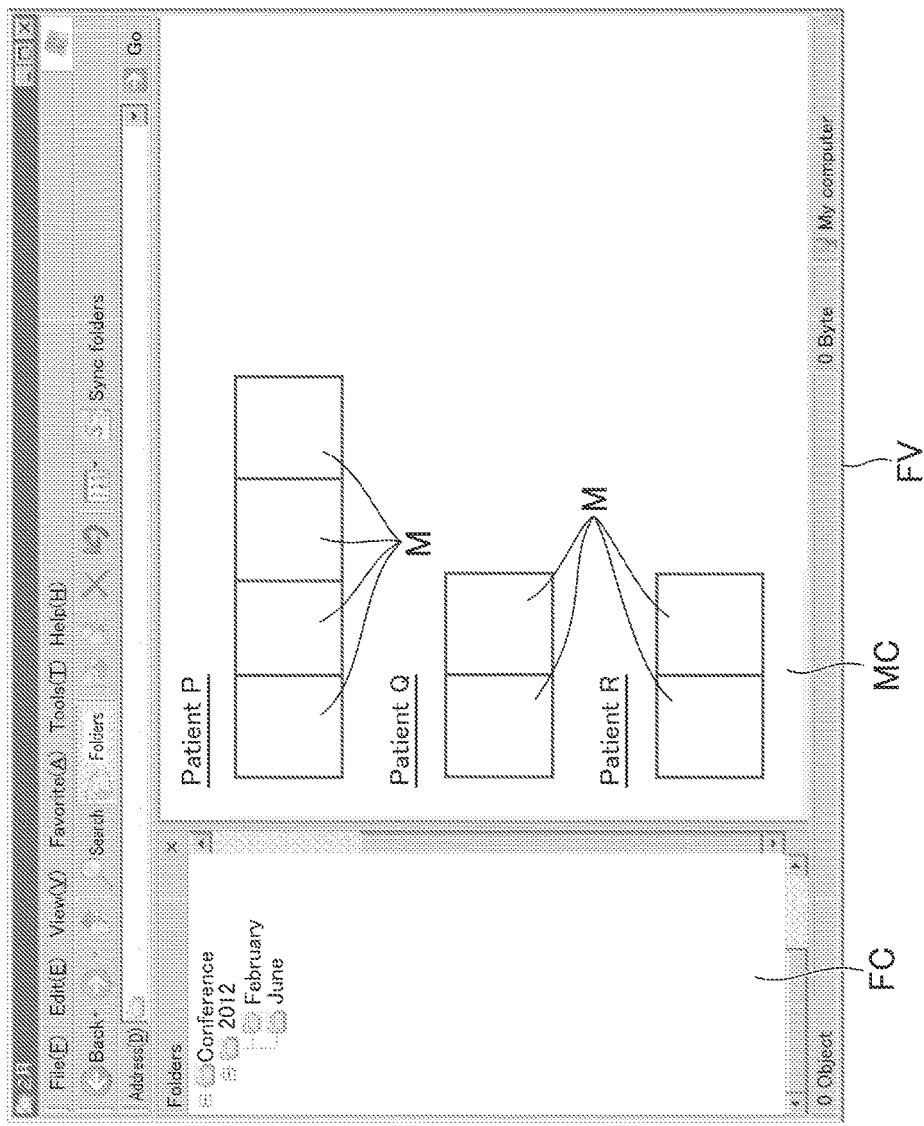
FIG. 21 shows a folder viewer.

The operator opens the "June" folder in a conference in June and displays images based on the simplified images M in the "June" folder to explain a case of a disease. In order to open the "June" folder, as shown in FIG. 21, the operator enters an input with the input unit 33 to display the folder viewer FV on the display screen 31a. The folder viewer FV includes a folder display field FC and a display field MC for the simplified images M.

The display of the folder viewer FV will be discussed below. When the operator enters an input to the input unit 33 to display the folder viewer FV, the data requesting unit 321 requests data on the folder viewer FV from the server 2. The display data creating unit 22 creates data on the folder viewer FV containing the simplified images M placed in the folder with reference to the table TA stored in the storage 21. The display data creating unit 22 creates data on the simplified images M contained in the folder viewer FV, based on medical data having UIDs in the table TA.

Moreover, the display data creating unit 22 creates data on the folder viewer FV containing the simplified images M classified patient. The display data creating unit 22 specifies patient names or patient IDs based on metadata with UIDs contained in the table TA, and classifies the simplified images M by patient. In FIG. 21, the simplified images M of patients P, Q, and R are classified and displayed on the display field MC of the simplified images.

The operator selects the "June" folder of the folder display field FC to display the simplified images M in the "June" folder on the display field MC of the simplified images. The operator then clicks on the simplified image M displayed in the display field MC of the simplified images. This causes the display screen 31a to display the images (original images), which is not particularly shown, based on medical data (the original data of the clicked simplified image M) stored in the storage 21 of the server 2. Thus, a case of a disease can be explained. During the explanation, the operator can compare a CT image used in a conference in February and a CT image newly obtained on May 18, 2012.

A click on the simplified image M outputs the UID of the simplified image M to the server 2. The data output unit 23 of the server 2 outputs medical data to the display terminal 3 according to the UID inputted from the display terminal 3. This allows an original image based on the medical data to be displayed on the display 31.

The present invention was described according to the embodiment. As a matter of course, the present invention can be modified in various ways within the scope of the present invention. For example, only the lengths of the first sub window SW1 and the second sub window SW2 need to extend in different directions (orientations). In other words, the orientations of the simplified images M in the first sub window SW1 only need to be different from those of the simplified images M in the second sub window SW2. For example, in the present embodiment, the first sub window SW1 is a vertically oriented rectangle while the second sub window SW2 is a horizontally oriented rectangle. Conversely, the first sub window SW1 may be a horizontally oriented rectangle while the second sub window SW2 may be a vertically oriented rectangle. In this case, the simplified images M are horizontally disposed in the horizontally oriented first sub window SW1 while the simplified images M are vertically disposed in the vertically oriented second sub window SW2. The lengths of the first sub window SW1 and the second sub window SW2 may be diagonally extended as long as the lengths are not in parallel with each other.

The first sub window SW1 and the second sub window SW2 may vary in shape and color.

In the present embodiment, the list of simplified images is displayed based on medical data. The present invention is not limited to medical data. The present invention is applicable to a display device that displays a list of images based on data containing associated information of multiple attributes as metadata, and an image display system. In the list, however, the simplified images need to be located for associated information of one attribute in the column direction and for associated information of another attribute in the row direction.

Figure 22:
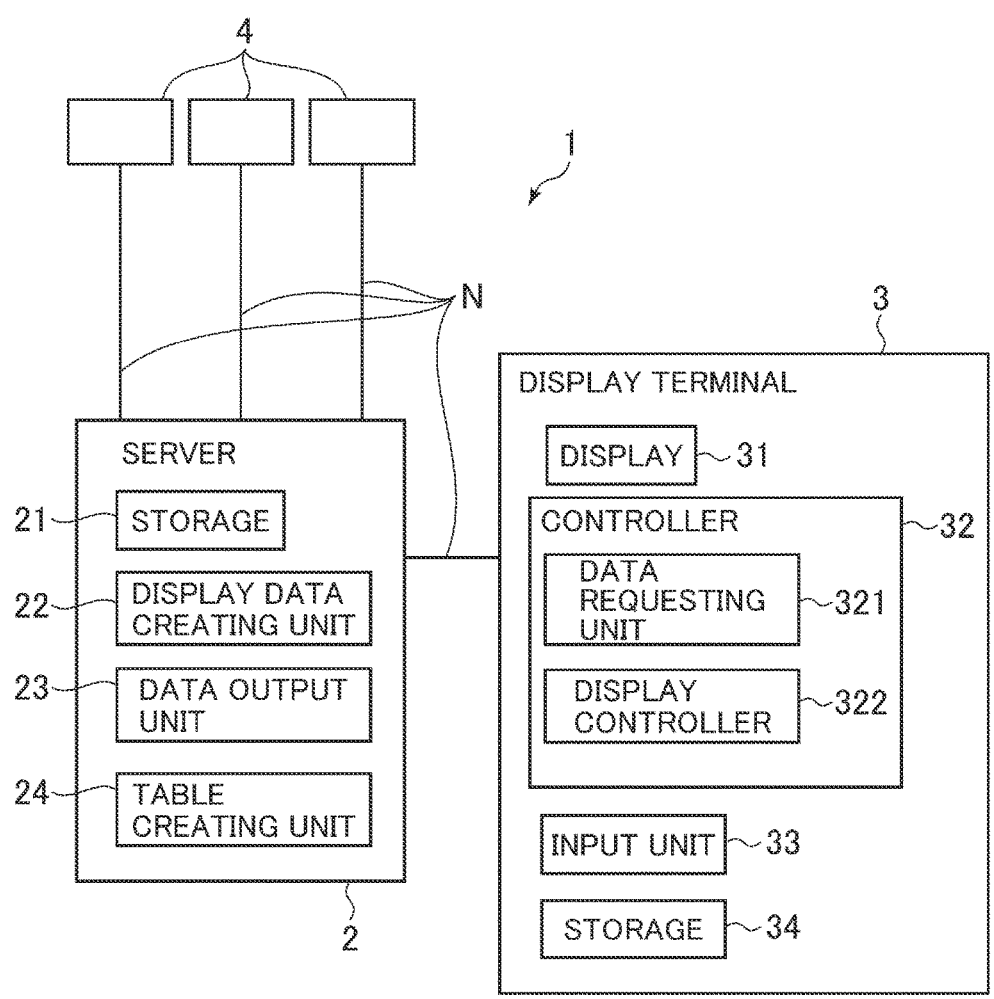
FIG. 22 is a block diagram showing another example of the image display system according to the embodiment.

As shown in FIG. 22, the table creating unit 323 provided in the display terminal 3 may be replaced with a table creating unit 24 in the server 2. In this case, dragging and dropping of the simplified image M into the folder outputs the UID of the simplified image M to the server 2 and then is written into $C_{UID}$ of the UID field of the table TA.

What is claimed is:

1. A display device comprising:
   a display terminal that displays a list of images in a matrix based on data containing associated information of multiple attributes as metadata, the images being located for respective pieces of associated information of one attribute in a row direction and respective pieces of associated information of another attribute in a column direction,
   wherein the display terminal displays a first window and a second window simultaneously on the list,
   the first window and the second window displayed in different display modes,
   the first window containing the images sharing the associated information of one attribute and the associated information of another attribute in the list of images,
   the second window containing the images selected from the images in the list and associated from a different point of view from the associated information in the list, the images contained in the second window being images which are placed into a same folder by means of an input unit.

2. The display device according to claim 1, wherein the first window and the second window are each shaped in one direction and are displayed in different directions.

3. The display device according to claim 1, wherein the images in the first window and the images in the second window are oriented in different directions.

4. The display device according to claim 1, wherein the display terminal has at least one first indicator that is displayed on the images shown in the first window in the list of images.

5. The display device according to claim 4, wherein the first window containing the images for the at least one first indicator is displayed on the display terminal in response to an input indicating the at least one first indicator.

6. The display device according to claim 5, wherein the at least one first indicator comprises a plurality of first indicators, an input indicating one of the first indicators displays the first window containing the images for the indicated first indicator, and an input indicating another one of the first indicators replaces, when the first window is displayed, the first window with another first window containing the images for the another one of the first indicators.

7. The display device according to claim 4, wherein the at least one first indicator includes the number of images in a cell that contains the images in the list.

8. The display device according to claim 1, wherein the display terminal has at least one second indicator that is displayed on the images shown in the second window in the list of images.

9. The display device according to claim 8, wherein the second window containing the images for the at least one second indicator is displayed on the display terminal in response to an input indicating the at least one second indicator.

10. The display device according to claim 9, wherein the at least one second indicator comprises a plurality of second indicators, an input indicating one of the second indicators displays the second window containing the images for the indicated second indicator, and an input indicating another one of the second indicators replaces, when the second window is displayed, the second window with another second window containing the images for the another one of the second indicators.

11. The display device according to claim 1, wherein an input on the list by an operator hides at least one of the first window and the second window.

12. The display device according to claim 11, wherein the input on the list is clicking or dragging and dropping on the list.

13. The display device according to claim 1, wherein the list is partially displayed on the display terminal, and an input for moving a part displayed on the display from the list hides at least one of the first window and the second window.

14. The display device according to claim 1, wherein the display terminal shows an indicator capable of distinguishing between the image placed in the folder and the image not placed in the folder, and the second window is displayed in response to an input on the indicator by the operator.

15. An image display system, comprising:
    a display device comprising:
      a display terminal that displays a list of images in a matrix based on data containing associated information of multiple attributes as metadata, the images being located for respective pieces of associated information of one attribute in a row direction and respective pieces of associated information of another attribute in a column direction, wherein the display terminal displays a first window and a second window simultaneously on the list, the first window and the second window displayed in different display modes, the first window containing the images sharing the associated information of one attribute and the associated information of another attribute in the list of images, the second window containing the images selected from the images and the list and associated from a different point of view from the associated information in the list, the images contained in the second window being images which are placed into a same folder by means of an input unit; and
    a server connected to the display device.

16. The image display system according to claim 15, wherein the server comprises a list creating unit that creates the list containing the first window and the second window.

17. The image display system according to claim 15, wherein the server comprises a storage that stores the data.

18. A computer-implemented method, comprising:
- displaying, by a display terminal, a list of images in a matrix based on data containing associated information of multiple attributes as metadata, the images being located for respective pieces of associated information of one attribute in a row direction and respective pieces of associated information of another attribute in a column direction, with each image representing a stored computer file; and
- displaying a first window and a second window simultaneously such that the first window and the second window overlie the list;
- wherein the first window and the second window are displayed in different display modes,
- the first window contains the images sharing the associated information of one attribute and the associated information of another attribute in the list of images, and
- the second window contains the images selected from the images in the list and associated from a different point of view from the associated information in the list, the images contained in the second window being images which are placed into a same folder by means of an input unit.

\* \* \* \* \*